(12) United States Patent
Tantawi et al.

(10) Patent No.: US 12,144,100 B2
(45) Date of Patent: Nov. 12, 2024

(54) 3D HIGH SPEED RF BEAM SCANNER FOR HADRON THERAPY

(71) Applicant: The Board of Trustees of the Leland Stanford Junior University, Stanford, CA (US)

(72) Inventors: Sami G. Tantawi, Stanford, CA (US); Emilio Nanni, Redwood City, CA (US); Zenghai Li, Stanford, CA (US); Cecile Limborg-Deprey, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 1055 days.

(21) Appl. No.: 17/006,742

(22) Filed: Aug. 28, 2020

(65) Prior Publication Data

US 2021/0060358 A1    Mar. 4, 2021

Related U.S. Application Data

(60) Provisional application No. 62/894,491, filed on Aug. 30, 2019.

(51) Int. Cl.
| | |
|---|---|
| *H05H 7/00* | (2006.01) |
| *A61N 5/10* | (2006.01) |
| *H05H 7/02* | (2006.01) |
| *H05H 7/04* | (2006.01) |

(52) U.S. Cl.
CPC .......... *H05H 7/001* (2013.01); *A61N 5/1043* (2013.01); *A61N 5/1077* (2013.01); *H05H 7/02* (2013.01); *H05H 7/04* (2013.01); *A61N 2005/1087* (2013.01); *H05H 2007/025* (2013.01); *H05H 2007/045* (2013.01)

(58) Field of Classification Search
CPC ............ H05H 7/001; H05H 7/02; H05H 7/04; H05H 7/18; H05H 2007/025; H05H 2007/045; H05H 2007/004; H05H 2007/007; H05H 2007/043; A61N 5/1043; A61N 5/1077; A61N 2005/1087
USPC ...................................................... 250/492.3
See application file for complete search history.

(56) References Cited

U.S. PATENT DOCUMENTS

| | | | |
|---|---|---|---|
| 7,554,275 B2 | 6/2009 | Amaldi | |
| 2007/0051905 A1* | 3/2007 | Fujimaki | G21K 1/10 250/503.1 |
| 2010/0320403 A1* | 12/2010 | Amaldi | A61N 5/10 250/492.3 |
| 2018/0256919 A1* | 9/2018 | Shen | A61N 5/1043 |

* cited by examiner

*Primary Examiner* — Kiet T Nguyen
(74) *Attorney, Agent, or Firm* — Kilpatrick Townsend & Stockton LLP

(57) ABSTRACT

A hadron therapy system that provides 3D scanning and rapid delivery of a high dose. Such systems can include a hadron source and accelerator with an RF energy modulator and an RF deflector that operate in combination to provide 3D scanning of a targeted tissue. The systems can include a permanent magnet quadrupole for magnification of the beam. The systems can include high energy hadron sources that utilize a multi-cell, multi-klystron design that achieves scanning of high energy hadron beams, for example a fixed energy of 200 MeV protons. Such systems can provide full irradiation of a liter scale tumor within one second or less.

14 Claims, 30 Drawing Sheets
(8 of 30 Drawing Sheet(s) Filed in Color)

d

3D HIGH SPEED RF BEAM SCANNER FOR HADRON THERAPY

CROSS-REFERENCES TO RELATED APPLICATIONS

This application claims the benefit of U.S. Provisional Patent Application No. 62/894,491, filed Aug. 30, 2019, which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under contract DE-AC02-76SF00515 awarded by the Department of Energy. The Government has certain rights in the invention.

BACKGROUND OF THE INVENTION

Treatment of cancer using hadron particle beams (protons and light ions) has significant advantages over treatments using photons. However, the accelerators as well as the gantries supporting the beam delivery systems are significantly larger and more expensive than conventional radiation therapy machines and gantries. Besides the obvious problems with size and cost with these large systems, the beam also has a slow energy scanning rate, which increases the overall treatment time and makes the treatment plan susceptible to patient motion. In addition, the full potential of these machines is compromised because the slow methods used to adjust beam energies, also introduce additional energy and momentum spread in the beam.

Modern active beam scanning systems reduce the amount of passive material in the beam by actively scanning pencil beams magnetically and changing their depth by changing the energy either at the accelerator (synchrotrons) or by using a variable range shifter with subsequent energy selection (cyclotrons). Again, the change in energy in multiple small steps is of the order of many hundreds of milliseconds to seconds per step and hundreds to thousands of those steps are needed during a treatment session.

Among the different commercial instruments providing pencil beam scanning, the ProBeam system (from Varian) offers one of the fastest layer switching capabilities. Beam delivery of 2 Gy/L/s (two Gy in one second over a one liter size volume) is achieved with the ProBeam system. It is the dose delivery rate also targeted for the TERA foundation system. However, there is need for improved treatment systems that provide for higher and even faster dose delivery. There is further need for such systems that are more compact in size and more economical than existing proton treatment system.

BRIEF SUMMARY OF THE INVENTION

The present invention pertains to particle therapy, in particular hadron therapy, notably therapy systems utilizing positively charged ions or protons.

In one aspect, the system of the present invention utilizes a compact beam delivery system capable of delivering protons or ion beams up to carbon with a rapid (seconds or less) 3D scanning over a tumor volume of up to 4 liters in both transverse and longitudinal dimensions. This is accomplished by introducing a relatively compact RF energy modulator followed by an RF deflector and a short permanent magnet quadrupole into the beam delivery system. Such a design can be implemented after any accelerator delivering a fixed energy proton/hadron beam. It provides a major clinical advantage when treating tumors affected by internal motion and provides a much higher patient throughput.

In some embodiments, the present invention utilizes RF energy modulation and deflection to enable a dose delivery of 50 Gy/L/s. Very fast irradiation presents many benefits to patients: (1) it solves the issue of patient motion and thus removes the need for tracking organ motion during irradiation (motion-adapted radiation therapy); it implies single- or hypofractionated treatments which (2) increases dramatically patient throughput and (3) presents biological benefits. In some embodiments, by using an RF based solution, switching times to tune the energy and position of the pencil beam sent to the patient are very fast. In some embodiments, switching times are reduces to a few seconds or less, typically within a second or less. With RF pulses at 1-10 kHz repetition rates inter-pulse changes can discretely adjust energy and deflection on the sub-ms timescale. Even faster switching can be achieved with intra-pulse changes to the RF amplitude and phase resulting in microsecond timescale adjustments.

To irradiate a tumor with 50 Gy/L/s, the source and accelerator upstream of the delivery system typically needs to provide at least $10^{13}$ hadrons in less than one second while matching the time structure of the RF. This requirement is well met by cyclotron sources with few mA, with 10 mA for synchrotrons and 0.5 mA for linacs. Each of the three types of hadron sources had their intensity performances pushed for physics applications and are good candidates for systems used in hadron therapy for cancer. In some embodiments, the system utilizes a linac designed for operation at 150 MeV or greater, typically 200 MeV (+/−3-MeV), for delivery of an entire irradiation dose in less than one second. In some embodiments, the system utilizes a ±30 MeV linac designed for operation at 200 MeV for rapid variation in depth at ~25 cm±6 cm, an RF deflector for rapid scanning, and a permanent magnet quadrupole to amplify the beams scanning area. The RF deflector and statically position quadrupole provides 25 cm×8 cm coverage. The permanent magnet quadrupole can be rotatable to provide increased coverage of a full 25 cm×25 cm area with 6 discrete steps in less than one second. These three components can provide this dynamic performance with a total length of 2 m, and make significant progress towards the goals set forth by the DOE-NCI workshop on Ion Beam Therapy by achieving penetration depths of >30 cm in water, rapid scanning with energy modulation over areas >20×20 cm, and a high enough dose of >20 Gy/L/s for hypofractionated treatments.

In another aspect, the high dose delivery can be demonstrated by upgrading of the beam source to match the RF time structure. This aspect allows for dose delivery of greater than 25 Gy/L/s, for example on the order of 50 Gy/L/s or greater. Treatment planning calculations with this technology can also be verified.

In yet another aspect, this approach can utilize RF technologies with components light and small enough to fit on a movable gantry. This allows the system to deliver the beam at the best angle for the patient and still fit in a treatment room. Note that for the implementation of this approach, a facility can operate with more than one beamline to accommodate multiple energy ranges each optimized for treating a certain body region (e.g., brain/head and neck, chest, abdomen & pelvis), with the goal of achieving higher patient throughput with cost/size savings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows simulated electric field; FIG. 5B shows mapping of distance S used to plot surface fields in FIGS. 5C and 5D; FIG. 5C shows electric field levels around the surface; and FIG. 5D shows magnetic field levels on the surface, in accordance with some embodiments.

FIGS. 26-27 graphically show estimation of an exemplary bunch length, in accordance with some embodiments.

DETAILED DESCRIPTION

The present invention can be further understood by the following detailed descriptions of various concepts and the accompanying figures noted above. It is understood that the invention is not limited to the following exemplary embodiments and that variations can be realized in accordance with the concepts described herein.

Figure 1:
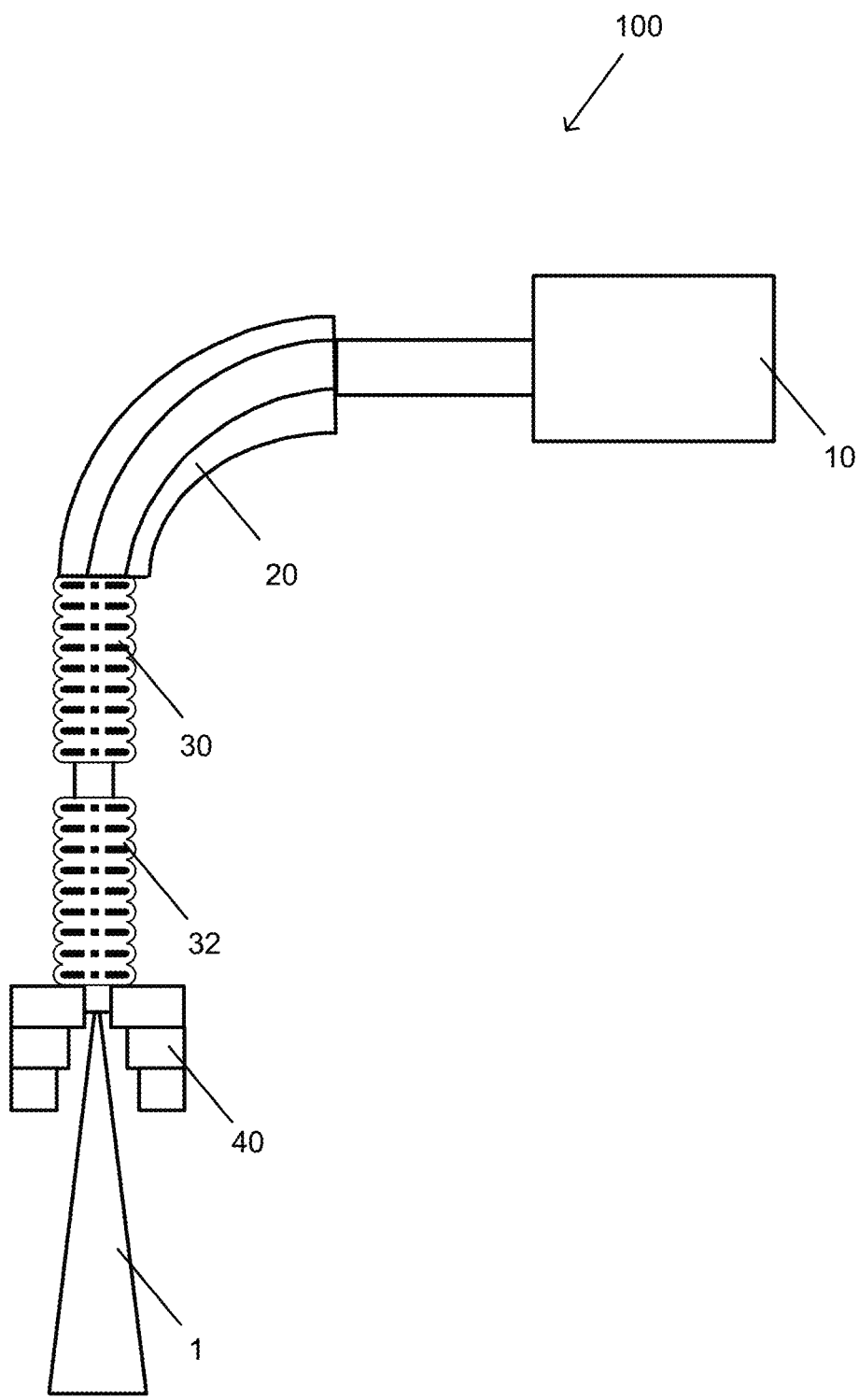
FIG. 1 shows an exemplary hadron therapy system in accordance with some embodiments of the invention.

FIG. 1 shows a schematic of an example gantry system 100. The system includes a hadron source/accelerator 10, transfer portion 20, RF energy modulator 30, RF deflector 32, and magnetic quadrupole 40. The gantry is fed by an accelerator delivering a fixed energy hadron beam and the RF structures operate to scan and deliver the hadron therapy beam 1 rapidly to the targeted tissue in the patient at a high dose. The hadron source/accelerator 10 is configured to deliver a hadron beam at a desired energy suitable for therapy 50-400 MeV. The transfer portion 20 transfers the hadron beam to the gantry, for example, by use of one or more permanent magnets that bend the hadron beam. The RF energy modulator 30 provides RF modulation within a desired range (e.g., +/−30 MeV). The magnet quadrupole 40 can include multiple permanent magnet quadrupoles, for example, the three magnet design shown. In one aspect, the gantry provides 3D-scanning by combining the RF energy modulation with the fast steering of RF deflector and magnification by the permanent magnet quadrupole. In some embodiments, the system achieves a 25 cm×25 cm scanning area with 12 cm depth variation in less than 1 second for a dose of 50 Gy/L/s or greater.

To scan the hadron beam transversally, the system utilizes an RF deflector. The RF deflector can be positioned after the ±30 MeV linac used as a fast energy modulator. One major advantage of using an RF deflector instead of magnetic steering is the very fast switching time, on the order of the RF fill time, less than one second (e.g., a microsecond scale). Fast 3D scanning allows full irradiation of liter scale tumors in less than one second.

In one aspect, the challenges in using an RF deflector are: (1) low $\beta=v/c$ particles drift much slower than the phase of the RF wave in the cavity, so to cumulate transverse kicks the RF wave must have the correct phase from cell to cell and the cell length must be optimized for the range of $\beta$ covered; (2) the power efficiency of the structure must be high enough to make the system light and compact; and (3) the kick produced should be large enough for the hadron beam to reach transverse positions of ±10 cm approximately 1 meter after the deflector, requiring kick angles of ~±100 mrad.

In regard to item (1), at SLAC, a new generation of high efficiency accelerator structures has been developed, the distributed coupling linac, in which each cell in the structure is fed separately through power distribution manifolds. This eliminates the need for careful consideration of the coupling between cells, affording the designer extra degrees of freedom to shape the cell and optimize the performance. This technique can be used for designing an improved type of deflector that consumes much less power and is capable of much higher deflection fields. This technique can be used in applications to shorten the bunch length operation for storage rings (see Z. Li, et. al., Normal conducting cw transverse crab cavity for producing short pulses in spear3," Proceedings of IPAC2017, Copenhagen, Denmark; incorporated herein by reference for all purposes).

In regard to items (2) and (3), these are evaluated together, since the two conflicting conditions require finding the best compromise. To produce a 100 mrad transverse kick, a transverse energy of ~3 MeV would be needed for a 220 MeV kinetic energy proton beam. In an RF cavity, the iris aperture needs to be sufficiently small to make the cavity power efficient. The quantity $a/\lambda$, where $\lambda=c/f_{RF}$ and a the iris radius, typically needs to be of the order of ~0.1 or less for the cavity to be efficient. So a 100 mrad cumulative kick can be very challenging unless very low frequency, bulky cavities are used. To counter this problem, the system utilizes an RF deflector which can provide discrete kicks up to ~10 mrad and then amplify the kick by using permanent magnets. A very good amplification (e.g., 10-100×) can be achieved by using a series of small bore permanent magnet quadrupoles. In some embodiments, the magnet pole tip has a magnetic field of 0.1-3 T (e.g. 1.4 T). The bore increases in three steps such that very high gradient fields can be achieved. For example, with a 28 cm long magnet the system can generate transverse kicks of up to 100 mrad for 230 MeV proton beams.

In one aspect, the system utilizes a low B hadron beam RF deflector together with the beamline components suitable to achieve the required transverse beam properties. This enables 3-D scanning of the tumor. In addition, simulations can be used to ensure that treatment plans solutions can be implemented.

Existing Proton Beam Therapy Systems

Typically, existing proton therapy equipment designs use either synchrotrons, which have an energy extraction system flexible enough for treating tumors, or fixed-energy cyclotrons with an energy selection system (ESS) comprised of energy degraders to provide flexible energy. Generally, upstream pencil beam scanning (PBS) system currently use conventional magnets to steer the beam laterally at each specific beam depth. Improved systems can utilize optimized resistive and superconducting magnets on the gantry to shrink the gantry size (diameter). The PBS system can treat a tumor in a 3D fashion such that the treatment plan is broken into discrete layers that correspond to the shape of the tumor at each depth within the body. As each layer dose is complete, the ESS can step the energy to the next lowest energy until each layer's treatment is completed.

Figure 2:
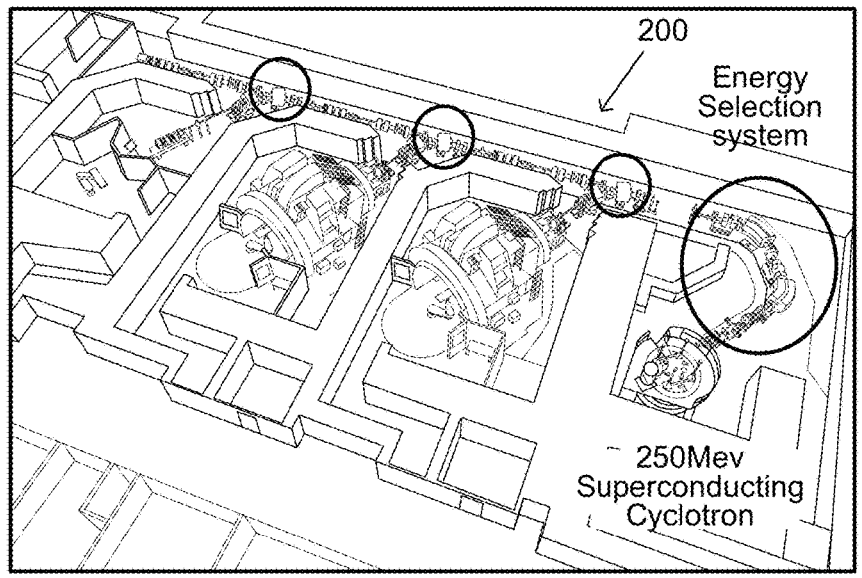
FIG. 2 shows conventional treatment systems in three treatment rooms.

FIG. 2 shows a schematic of a typical Varian ProBeam design 200, showing a layout with three treatment rooms (two gantry and 1 fixed beam) and associated beamline elements. This graphic also shows the beam element arrangement for the Energy Selection System for the main beamline (larger circle) and the individual room beamlines (smaller circles). The ProBeam system uses a degrader based Energy Selection System (ESS), and associated main beamline to manage the beam switching between each of the treatment rooms. This system is a cyclotron based proton machine, using a compact superconducting cyclotron that accelerates the protons to a fixed 250 MeV energy. After the proton beam is extracted into the treatment line, it first passes through the ESS which reduces the proton beam energy to the energy needed for each treatment depth or layer. The ProBeam ESS, for example, can generate beam energies from 245 MeV to 70 MeV. For the lowest cost system, i.e., a compact single room treatment system, the ESS can be integrated onto the actual gantry. The beamline is then straight out of the accelerator into the ESS on the gantry. For multi-room systems, there are beam kicker magnets (smaller circles in FIG. 2) to steer the proton beam into the treatment room being used for clinical treatment. The ESS can be configured either one per facility, as shown above, or there can be one ESS for each treatment room. The ProBeam system, as most degrader based ESS systems, uses mechanical motion to adjust the beam energy, hence the 3D scanning of the beam is slowed by having to move the degrader to its new position, as well as by adjusting all of the beamline magnets to the new energy selection.

Application of Recent SLAC RF Technology Advances to Proton Beams

Recent research has dramatically improved the performance in gradient and efficiency of accelerators by pursuing a deeper understanding of the basic physics of breakdown phenomena in high vacuum RF structures. This knowledge of geometrical effects and material properties to develop accelerator structures that require less power and operate with fields well above the present state of the art. The geometrical effects led allow use of completely novel topologies for accelerator structures, with methodologies that are different from the conventional approaches. This knowledge informs and be integrated within algorithms and design codes that allow very rapid optimization of RF structures for a particular application being designed for, with confidence in the operational performance of the device.

Figure 3:
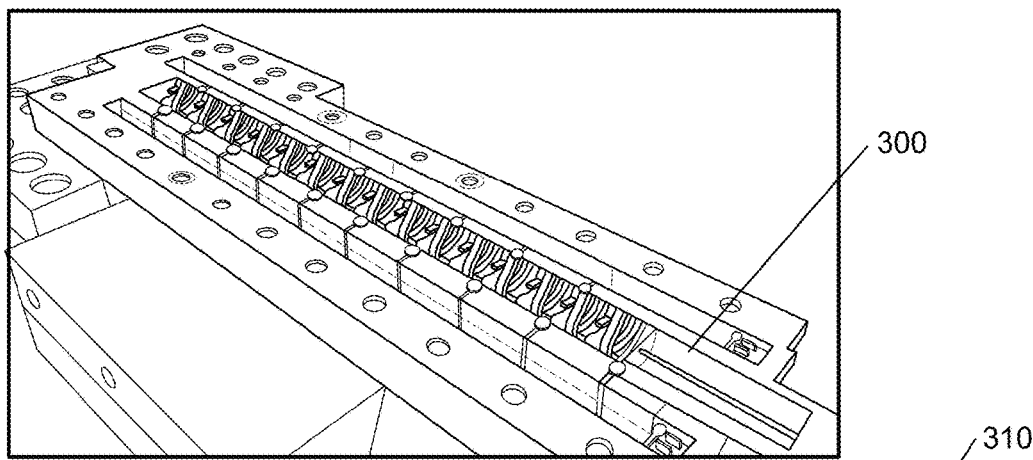
FIG. 3 shows an RF structure with a two manifold system (at top) and a fabricated and assembled accelerator (at bottom), in accordance with some embodiments.
Figure 3:
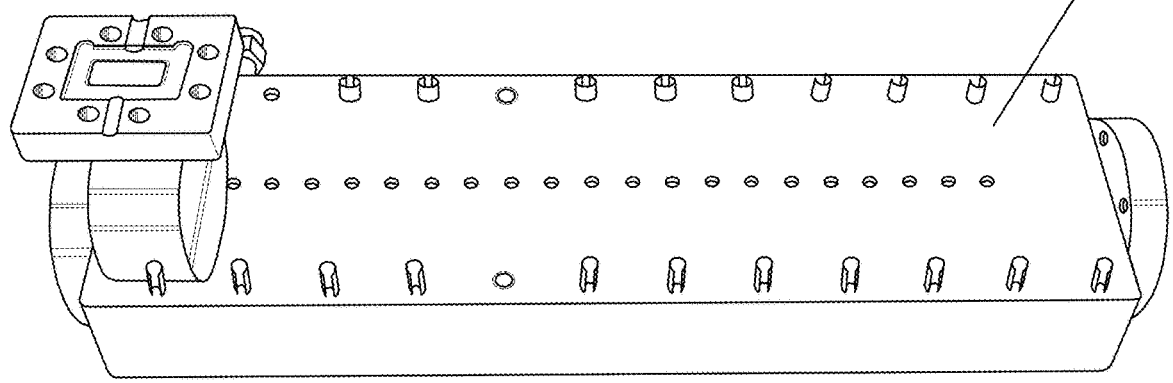

FIG. 3 shows RF structure with a two manifold system 300 for feeding every cell in a I-mode accelerator structure and a fabricated and assembled accelerator 310. These new topologies shown in FIG. 3 feed each cell or group of cells in the RF structure independently. These $\beta=1$ structures with individual power feeds have been tested successfully up to a 145 MV/m gradient with beam acceleration. Note that this design is for an operating frequency of 11.4 GHz, although it is appreciated that this design is suitable for various frequencies and can be designed for various differing parameters desired. This design methodology can be extended to any frequency and also for low beta structures (e.g., β=0.56 for 200 MeV protons).

In one aspect, the single cell feeding allows adjusting the phase to match the low β of the hadron beam. These topologies provide the highest possible shunt impedance and relax the demands on peak power required for a given field. They provide the uncoupling of the individual cells and controlling of the phase of each cavity and provide another degree of freedom when designing for RF structures uses, such as the one proposed herein for the RF deflector.

Figure 4A:
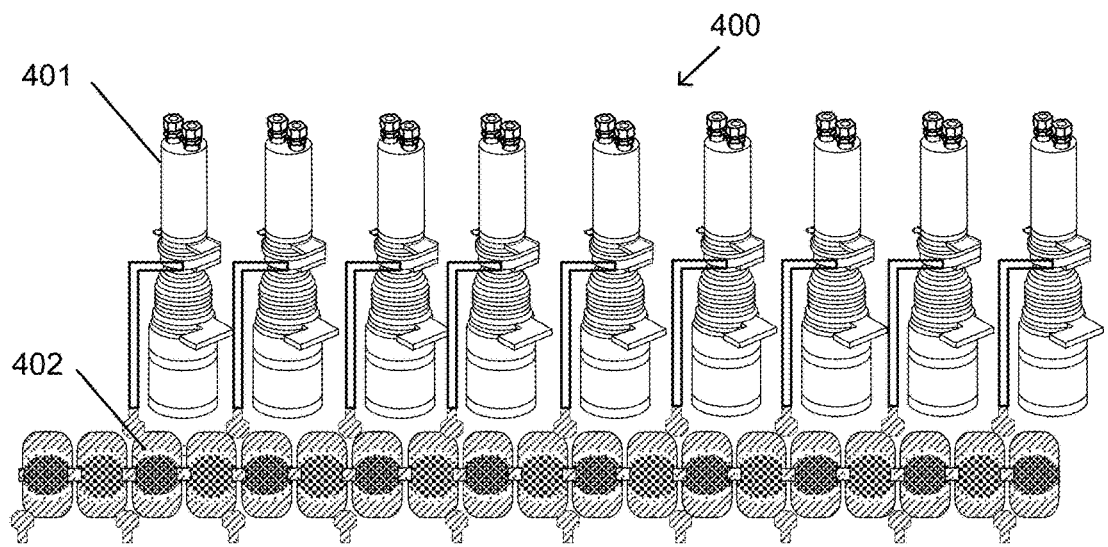
FIG. 4A shows powering of the RF structure with one klystron feeding one cell, in accordance with some embodiments.
Figure 4B:
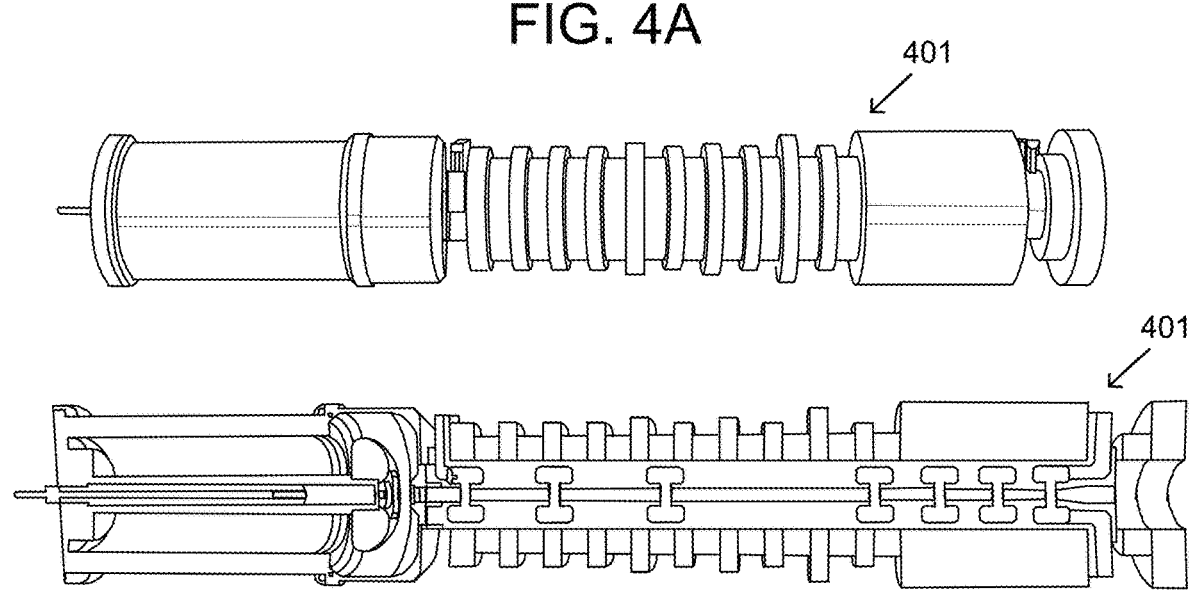
FIG. 4B shows each single unit klystron, in accordance with some embodiments.

In addition to the novel high field and high efficiency structures, the system can also utilize designs for high efficiency, compact klystrons and RF distribution systems. An example of a system are individual low voltage (60 kV) klystrons that produce ~300 kW at 60% efficiency is shown in FIG. 4A-4B. FIG. 4A illustrates powering of the RF structure 400 with one klystron 401 feeding one cell 402; FIG. 4B illustrates each single unit klystron 401 can provide 300 kW and has a 10 cm×10 cm footprint. These klystrons can individually power cells as depicted in FIGS. 4A-4B or use compact RF distribution networks for reaching higher peak powers when needed. In some embodiments, single klystrons are used to individually power cells and optimized phasing of klystrons to accelerate or transversally kick the low β beam. In some embodiments, systems can utilize RF sources delivering 300 kW with a very small footprint (10 cm×10 cm).

Exemplary Design of the RF Modulator

Figures 5A, 5B:
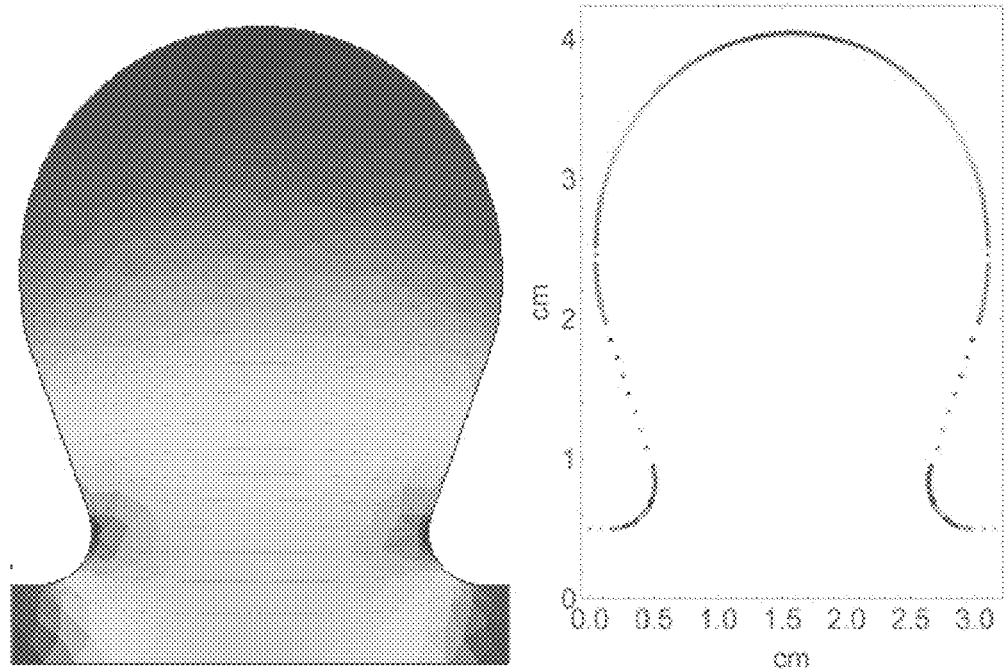
FIGS. 5A-5D show simulations of an S-band optimized cavity for use in a proton therapy system, in particular.
Figures 5C, 5D:
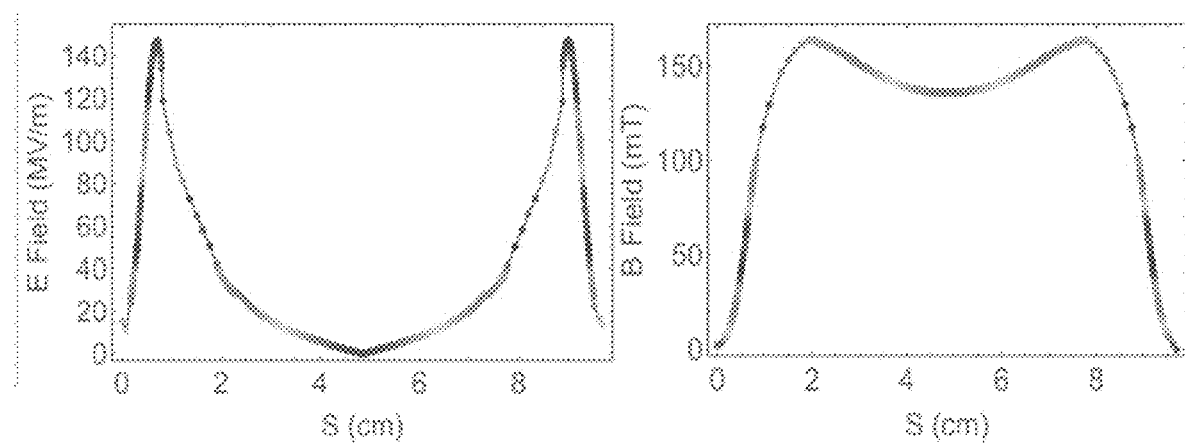

In an exemplary embodiment, the first RF structure that interacts with the proton beam on the gantry is the energy modulator, which can accelerate or decelerate the beam. Preliminary calculations for the cavities in the energy modulator with field levels are indicated in FIGS. 5A-5D. The shunt impedance of this cavity, defined as $R_s=G^2/P$, where G is the acceleration gradient and P is the power consumed per unit length, is ~60 MΩ/m. For an accelerating field of 25 MV/m, the peak electric field is ~72.5 MΩ/m. With this shunt impedance the RF power needed for a 1.2 meter 30 MeV S-band accelerator (40 cells) for a 200 MeV proton beam energy is ~12.5 MW corresponding to ~300 kW per cell. It is appreciated that a fully optimized system can perform even better. This approach is a particularly advantageous operating point because it provides both a compact linac, as well as a power requirement that a single efficient klystron at power levels >300 kW can provide with the designs currently being developed at SLAC and shown in FIG. 4. FIGS. 5A-5D show simulations of the S-band optimized cavity for 200 MeV protons. Field levels are calculated for 50 MV/m net acceleration: FIG. 5A shows simulated electric field; FIG. 5B shows mapping of distance S used to plot surface fields in FIGS. 5C and 5D; FIG. 5C shows electric field levels around the surface; and FIG. 5D shows magnetic field levels on the surface.

Exemplary Design of the RF Deflector

Figure 6:
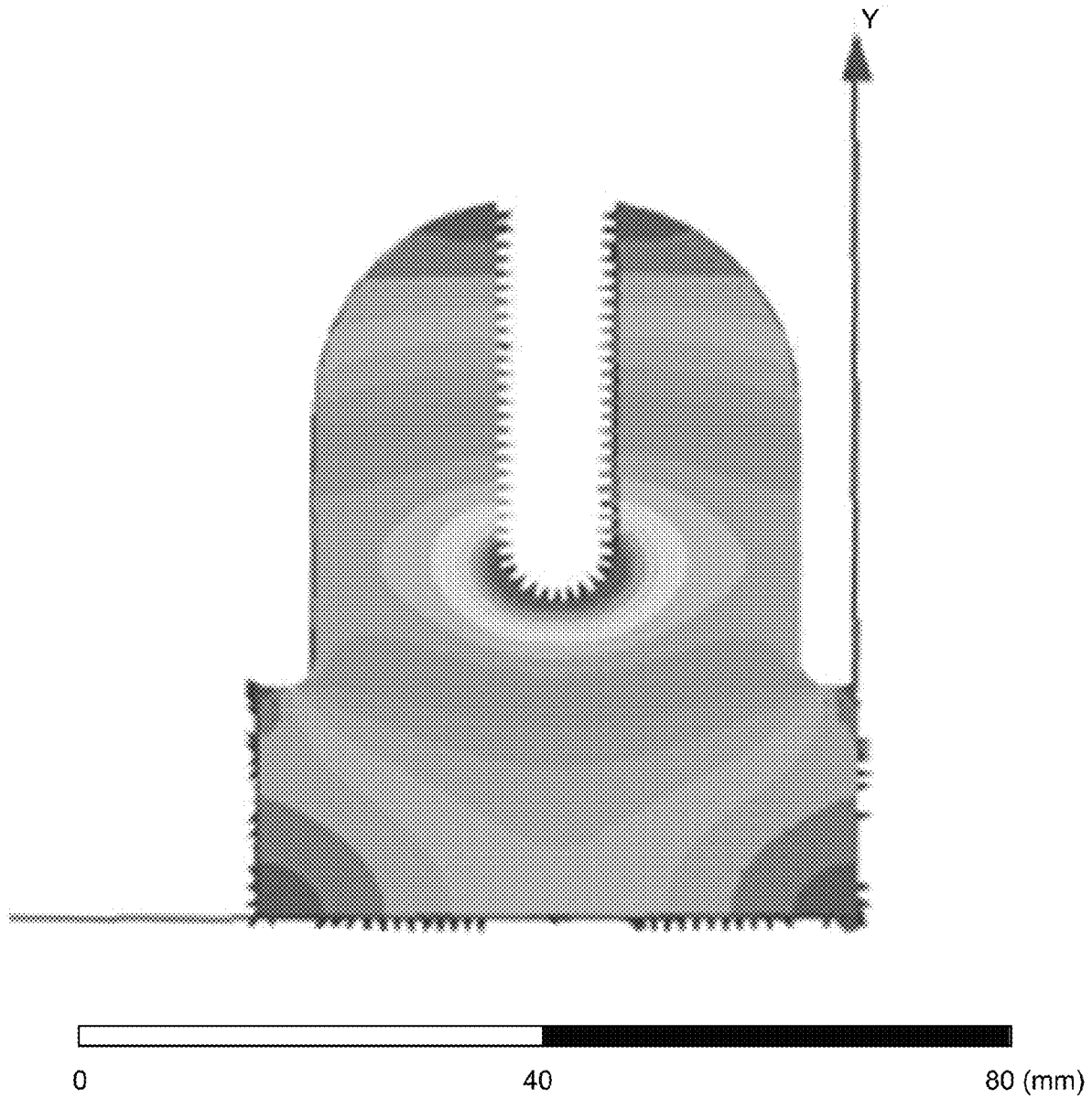
FIG. 6 shows deflecting cell geometry and simulated electric fields, in accordance with some embodiments.

Preliminary calculations to evaluate deflecting field amplitudes that can be achieved for a single proton in an optimized S-band structure, as shown in FIG. 6, for a cavity length of ~0.3λ, with λ=c/f, c being the speed of light and f the rf frequency. With a maximum peak surface field of 50 MV/m, the overall length of the cavity can be 0.5 m. A 4 MW total power is required for the transverse kick producing a 10 mrad angle and 10 mm offset at the exit. A power of 266 kW per klystron per cell can be required for each of the 15 cells in a distribution similar to what is shown in FIG. 4.

In some embodiments, the klystrons and RF structure can be fit into a 50 cm×50 cm cross-section box. This size enclosure for the linac and klystrons can fit onto a contemporary gantry in a proton therapy system. Typically, the cavity has a circular symmetry and hence both polarizations of the deflecting mode can be excited, making scanning in two dimensions possible. FIG. 6 illustrates deflecting cell geometry and simulated electric fields of the exemplary RF deflector.

Permanent Magnet Magnifying System

With +/−10 mrad divergence coming out of the RF deflector, it would require a 10 m drift for the proton beam to cover +/−10 cm at the target. In some embodiments, the system utilizes a magnet to magnify the transverse offset and angular spread produced by the RF deflector to allow coverage of a 20 cm diameter disk cross-section on the target while reducing the distance from the deflector exit to the target to approximately 1 m.

In some embodiments, the RF deflector is designed to achieve a circular field size of 20 cm for the hadron therapy beam line. With further optimization, larger field sizes can be achieved. In addition, larger field sizes are possible by seamless field patching moving the patient, a technique that has been optimized in modern treatment planning systems.

Figure 7:
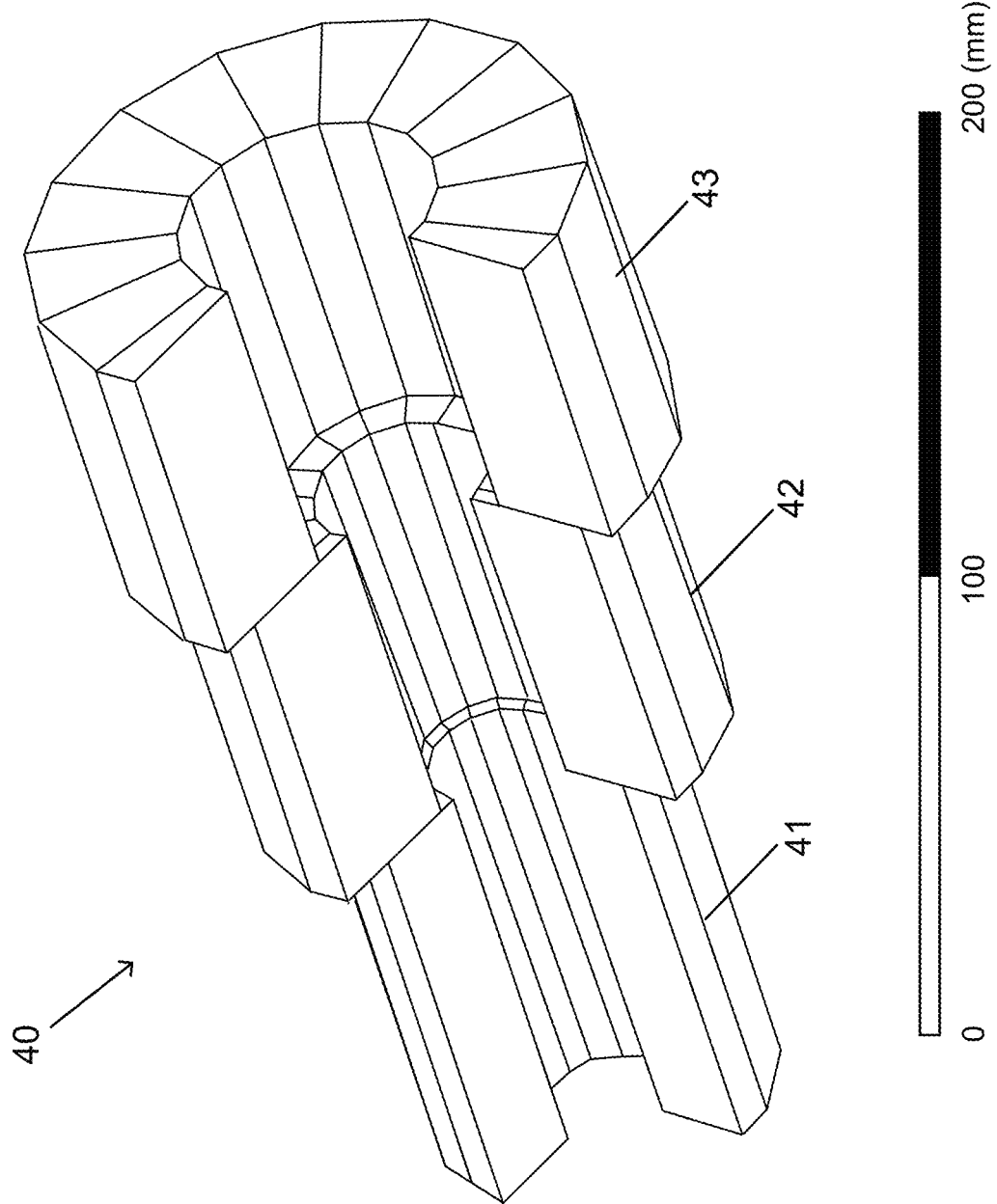
FIG. 7 shows a schematic of a stacked quadrupole for use in a hadron therapy system, in accordance with some embodiments.

One proposed solution is to use a magnet comprising a stack of high gradient permanent magnet quadrupoles. In an exemplary embodiment, the magnet comprises three short, very high gradient permanent magnet quadrupoles stacked together. FIG. 7 shows a schematic of such a magnet 40 comprised of a stack of three short permanent magnet quadrupoles 41, 42, 43 with increasing bore diameter—each made of 16 blocks of neodymium iron. Each quadrupole can be made following the procedure from K. Halbach. The inner radius of the quadrupole increases in three steps along the length, as shown in FIG. 7, to allow the diverging beam to pass through and maximize the magnetic field. Calculations show that assuming a 1.4 T pole tip for the three permanent magnet quadrupoles (PMQs), the 28 cm long magnet, weighing 85 kg, provides adequate fields. PMQs with 1.4 T pole tip have been built and used with charged particle beams.

Figures 8A, 8B:
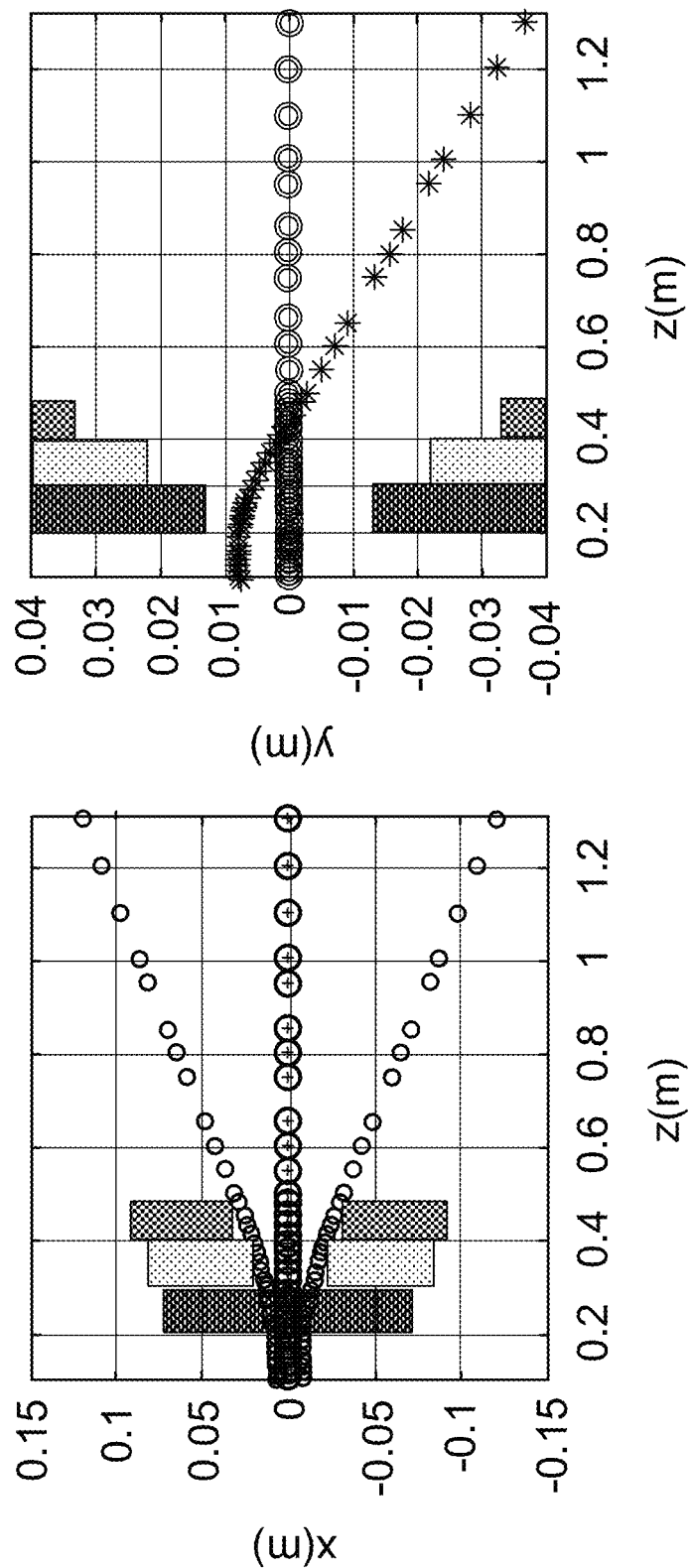
FIGS. 8A and 8B show horizontal and vertical trajectories, respectively, for the photon beams provided by an exemplary system, in accordance with some embodiments.

A 230 MeV proton beam exiting the RF deflector with centroids located at a position $x_o$ mm can have an angle of $x_o$ mrad. For $x_o=+/-7.5$. Calculations indicate that the magnet system deflects the proton beamlet up to +/−120 mrad such that the range covered is then +/−12.5 cm on the target at 1.1-m from the entrance of the magnet. Exemplary trajectories are shown in FIGS. 8A-8B for both the horizontal (x) and vertical (y) planes, respectively. FIG. 8A shows horizontal trajectories for the proton beam as the offset $x_o$ mm and divergence $x_o$ mrad is varied—blue is $x_o=7.5$, magenta is $x_o=-7.5$. FIG. 8B shows vertical trajectories for the proton beam as the offset and divergence is varied-red is $y_o=7.5$. The strong over-focusing happening in the vertical direction sends the beam to −4 cm when starting at $y_o=+7.5$ mm.

Figure 9:
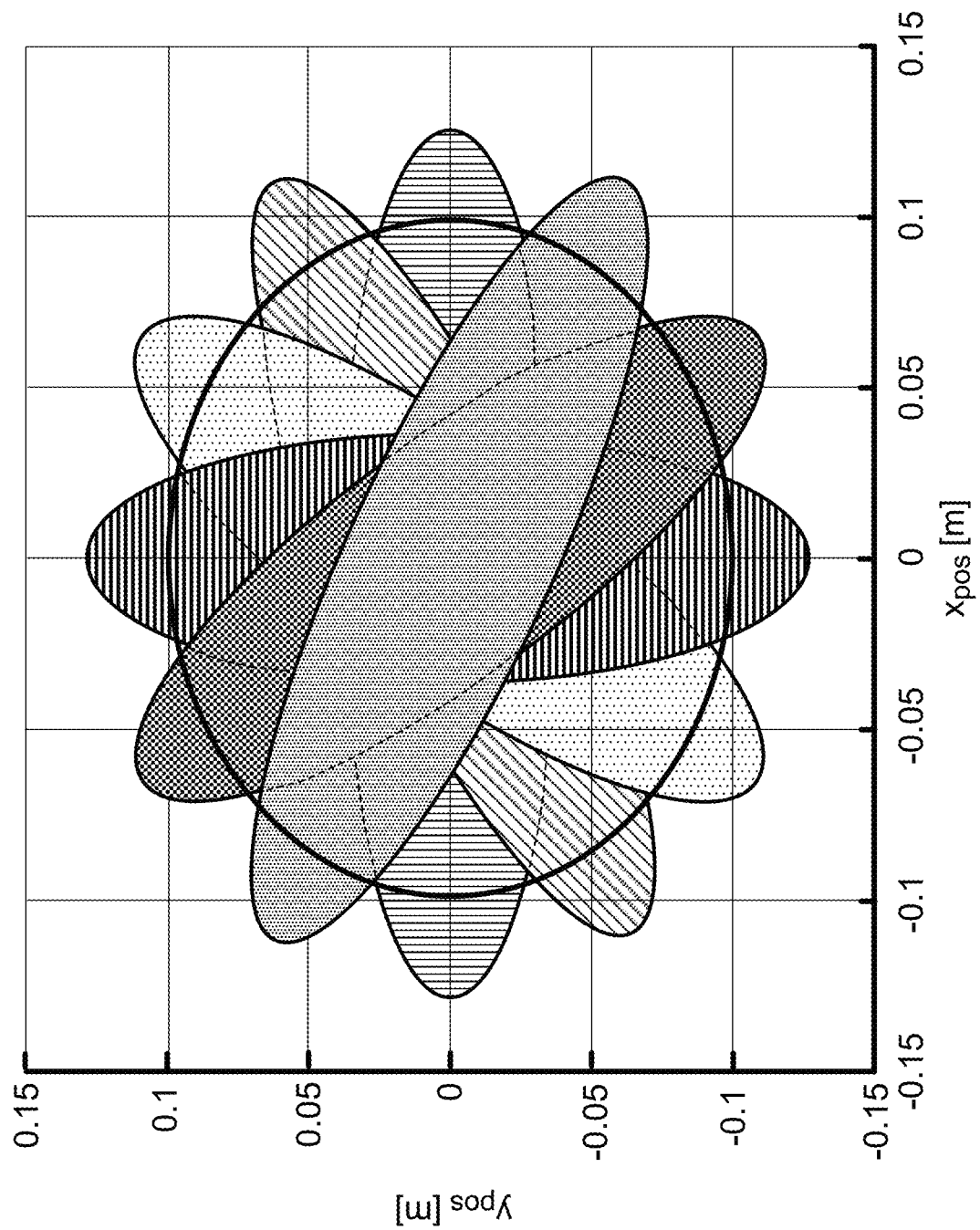
FIG. 9 shows areas covered on the target for six different positions of the magnet to provide complete coverage in the central circled region, in accordance with some embodiments.

Assuming a spread of the pencil beam to 4-mm FHWM at the target, a discretization of 62 points×20 points is needed to cover the entire elliptical surface area of 25 cm by 8 cm as shown for the blue elliptical surface in FIG. 9. So, 1240 pencil beams will be needed. In order to irradiate to the desired stopping at the edge of the tumor the energy can be varied as needed for each particular angle. The required field in the RF deflector can be adjusted to meet the angle and stopping distance requirements. The energy modulator and deflector RF parameters can be calculated to deposit the desired energy to the tumor volume in less than one second.

For tumor sizes exceeding the volume covered with a single position of the magnet, irradiation can be performed as the magnet is rotated. FIG. 9 shows that positioning the magnet at six angles can allow covering a disk of 20 cm diameter. As shown, six different positions of the magnet cover the target to provide entire coverage for a smaller disc portion at center.

As the energy of the proton beam is scanned to cover the depth of the tumor, the extreme position/angle at the exit of the RF deflector can be adapted since the beam angles can be increased for lower energy protons in the presence of fixed magnetic fields. The energy scanning can be interlaced into the radial scanning. The radial scanning can be interlaced in the azimuthal scanning. The optimization of this system to achieve compactness and reduced cost is yet another advantage of the system design described herein.

Compatibility with the Current Systems and Plans for Integration

In another aspect, these concepts are compatible for use with current treatment systems in order to provide the improvements described herein. For example, Varian Medical Systems currently has two ProBeam proton therapy installations, which can be used for testing of new treatment plans and plan verification. The TOPAS simulation platform allows to implement phase space outputs. The research room design implementation can permit the addition of magnetic systems and to test and verify beam deceleration and beam deflection prototype implementation and fast scanning and dose deposition solutions.

The following references describes various aspects of conventional system and concepts pertinent to the present invention and are therefore incorporated herein by reference in their entireties for all purposes:

[1] Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/2
[2] V. Anferov, M. Ball, G. P. Berg, B. Broderick, J. Collins, G. East, D. Friesel, D. Jenner, W. P. Jones, J. Katuin, S. Klein, C. Nelson, N. Schreuder, Wm. Starks, J. Self, "THE INDIANA UNIVERSITY MIDWEST PROTON RADIATION INSTITUTE", Proceedings of the 2001 Particle Accelerator Conference, (2001) p. 645-64, https://accelconf.web.cern.ch/accelconf/p01/PAPERS/FOAA004.PDF
[3] Th. Haberer, W. Becher, D. Schardt, G. Kraft "Magnetic scanning system for heavy ion therapy" Nuclear Instruments and Methods in Physics Research Section A: Accelerators, Spectrometers, Detectors and Associated Equipment, NIM, Elsevie, Jun. 10, 1993, Volume 330, Issues 1-2, 10 Jun. 1993, Pages 296-305
[4] PROTON AND CARBON LINACS FOR HADRON THERAPY U. Amaldi, TERA Foundation, Novara, Italy A. Degiovanni, CERN, Geneva, Switzerland Linac 2014 http://accelconf.web.cern.ch/AccelConf/LINAC2014/papers/friob02.pdf
[5] Montay-Gruel P, Petersson K, Jaccard M, Boivin G, Germond J F, Petit B, Doenlen R, Favaudon V, Bochud F, Bailat C, Bourhis J, Vozenin M C. Irradiation in a flash: Unique sparing of memory in mice after whole brain irradiation with dose rates above 100 Gy/s. Radiother Oncol. 2017 May 22. pii: S0167-8140(17)30365-1. doi: 10.1016/j.radonc.2017.05.003. [Epub ahead of print] PubMed PMID: 28545957.
[6] Favaudon V, Caplier L, Monceau V, Pouzoulet F, Sayarath M, Fouillade C, Poupon M F, Brito I, Hupé P, Bourhis J, Hall J, Fontaine J J, Vozenin M C. Ultrahigh dose-rate FLASH irradiation increases the differential response between normal and tumor tissue in mice. Sci Transl Med. 2014 Jul. 16; 6(245):245ra93. doi: 10.1126/scitranslmed.3008973. PubMed PMID: 25031268.
[7] Loo B W, Schuler E, Lartey F M, Rafat M, King G J, Trovati S, Koong A C, Maxim P G. Delivery of Ultra-Rapid Flash Radiation Therapy and Demonstration of Normal Tissue Sparing After Abdominal Irradiation of Mice. INTERNATIONAL JOURNAL OF RADIATION ONCOLOGY BIOLOGY PHYSICS. Volume: 98 Issue: 2 Pages: E16-E16 Supplement: S Meeting Abstract: P003 Published: Jun. 1, 2017
[8] M. Bopp, H. Fitze, P. Sigg, and L. Stingelin "Upgrade concepts of the PSI accelerator RF systems for a projected 3 mA operation", Citation: AIP Conference Proceedings 600, 300 (2001); doi: 10.1063/1.1435259
[9] K. Peach, et al. "PAMELA-A MODEL FOR AN FFAG BASED HADRON THERAPY MACHINE", Proceedings of PAC07, Albuquerque, New Mexico, USA
[10] S. Benedetti, A. Grudiev, and A. Latina " " Phys. Rev. Accel. Beams 20, 040101—Published 13 Apr. 2017
[11] The normalized (at peak) Bragg Curves for Various Proton Incident Energies in Water Phantom: A simulation with GEANT4 Monte Carlo Code, Abstract ID 8159, www.aapm.org/meetings/amos2/pdf.
[12] Z. Li, et. al., Normal conducting cw transverse crab cavity for producing short pulses in spear3," Proceedings of IPAC2017, Copenhagen, Denmark
[13] Valery Dolgashev, Sami Tantawi, Yasuo Higashi, Bruno Spataro, "Geometric dependence of radio-frequency breakdown in normal conducting accelerating structures," Applied Physics Letters, Volume 97, Issue 17, pp 171501-171501-3, October 2010.
[14] Lisa Laurent, Sami Tantawi, Valery Dolgashev, Chris Nantista, Yasuo Higashi, Markus Aicheler, Samuli Heikkinen, and Walter Wuensch, "Experimental Study of RF Pulsed Heating Phys. Rev. ST Accel. Beams 14, 041001 (2011) [21 pages]
[15] S. Tantawi, Z. Li, patent pending, Title: "Distributed Coupling and Multi-Frequency Microwave Accelerators", Filed: Jul. 9, 2014, Appl. No. 62/022,469
[16] S. Tantawi, M. Nasr, "Designs and High Power Tests of Distributed Coupling Linacs" IFIC, 13-16 Jun. 2017, Valencia, Spain https://indico.cern.ch/event/589548/contributions/2615455/attachments/1479738/2294080/Mamdouh_High_Gradient_2017.pdf
[17] Jensen, Aaron, Jeff Neilson, and Sami Tantawi. "X-band multi-beam klystron design and progress report." Vacuum Electronics Conference (IVEC), 2015 IEEE International. IEEE, 2015
[18] K. Halbach, "Design of permanent multipole magnets with oriented rare earth cobalt material", Nuclear Instruments and Methods, Volume 169, Issue 1, 1 Feb. 1980, Pages 1-10 [http://www.sciencedirect.com/science/article/pii/0029554X80900944].
[19] Lim, et al., "Adjustable, short focal length permanent-magnet quadrupole based electron beam final focus system" Phys. Rev. ST Accel. Beams 8, 072401-Published 15 Jul. 2005

Although FIG. 1 shows the major gantry components of an exemplary system, it is appreciated that the gantry can include various other components not shown. For example, the system can include additional features, not shown, including energy modulation cavities, thermals, beam dynamics, a cyclotron, bunch compression and gantry layout features. The following figures depict structures that can be utilized in a hadron therapy system in accordance with the concepts described herein. While these structures have been designed to provide certain characteristics, it is appreciated that these designs are not so limited and can be designed to according to various other parameters as needed for differing system requirements and energy levels as desired.

Figure 10A:
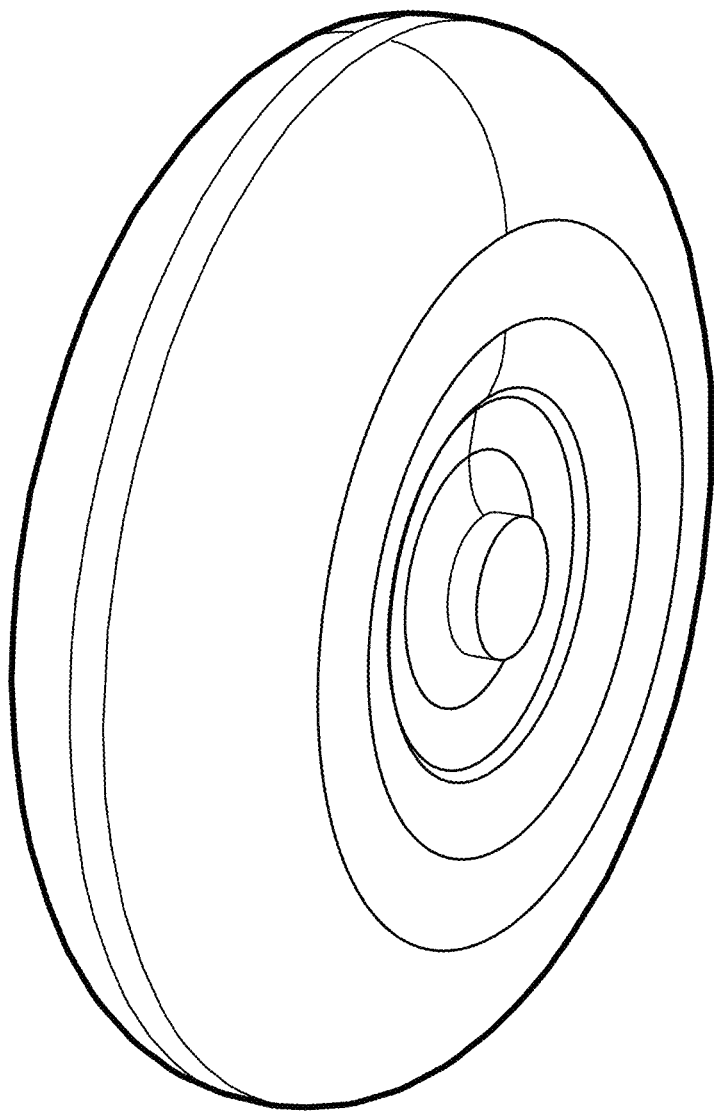
FIG. 10A shows an exemplary energy modulation cavity design for use in a therapy system, in accordance with some embodiments.
Figure 10B:
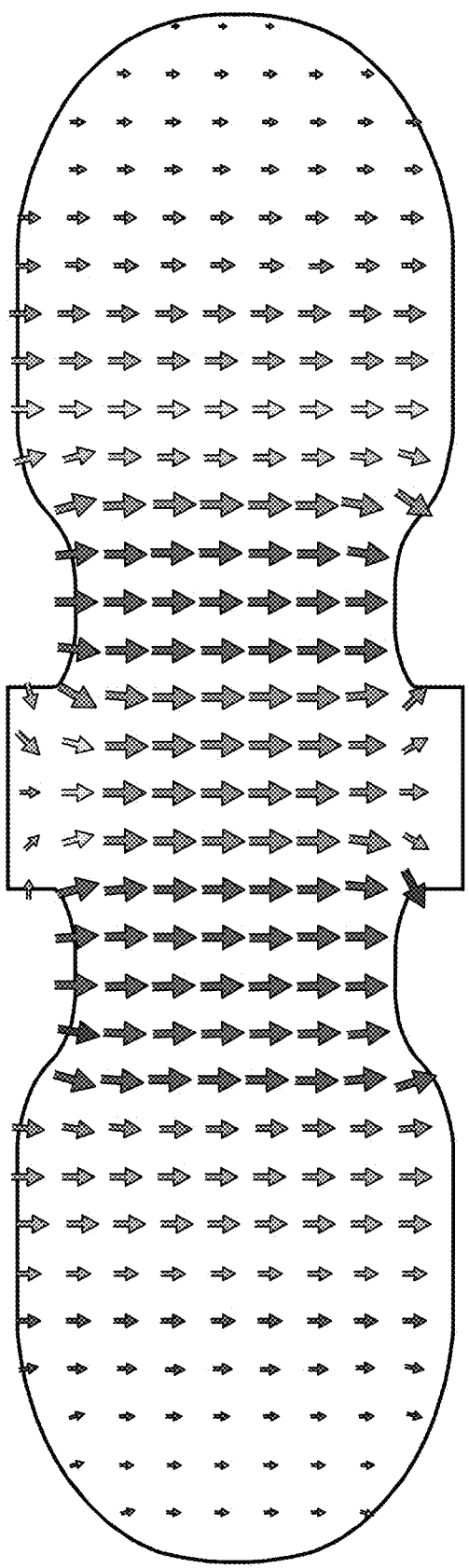
FIG. 10B shows the electric field distribution in the cavity design of FIG. 10A.

FIG. 10A shows an exemplary energy modulation cavity design 1000 for use in a therapy system, in accordance with some embodiments. FIG. 10B shows the electric field distribution in the cavity design of FIG. 10A.

Figure 11A:
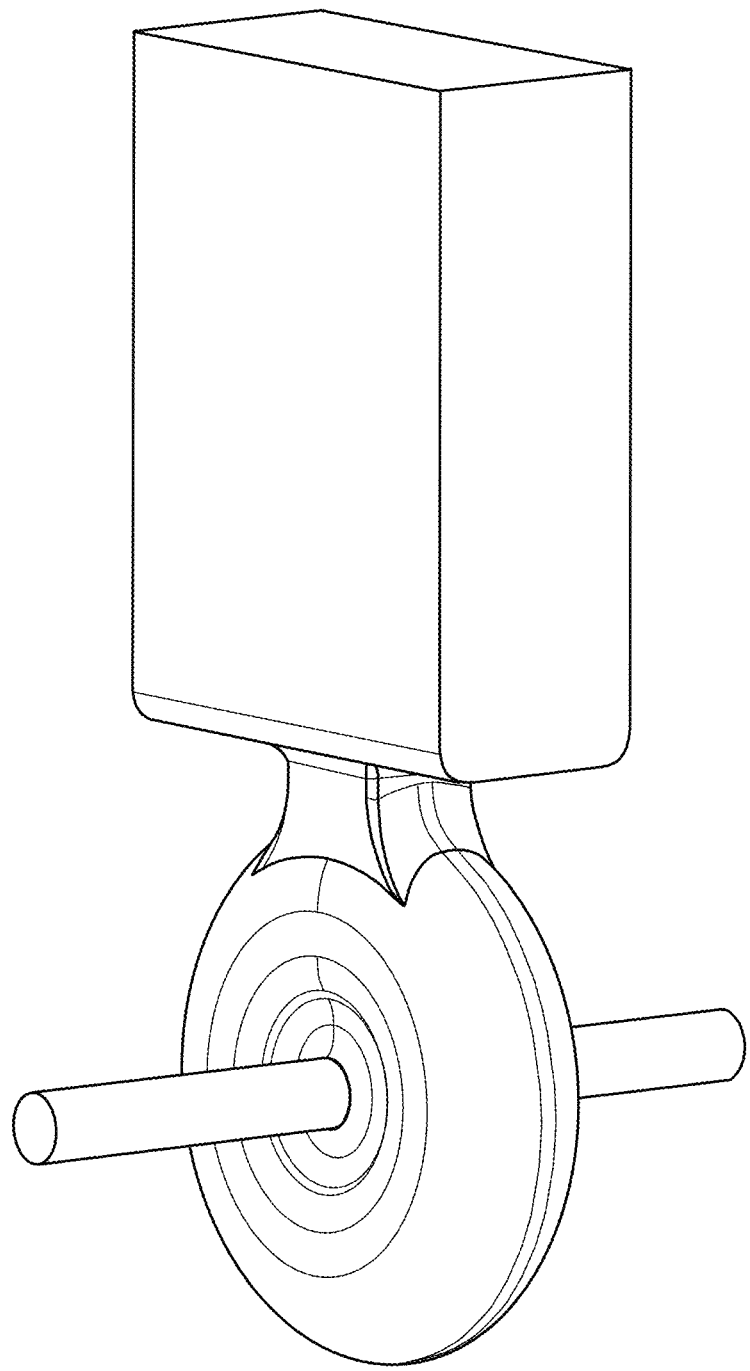
FIG. 11A shows an exemplary proton cavity with coupler for use in a therapy system, in accordance with some embodiments.
Figure 11B:
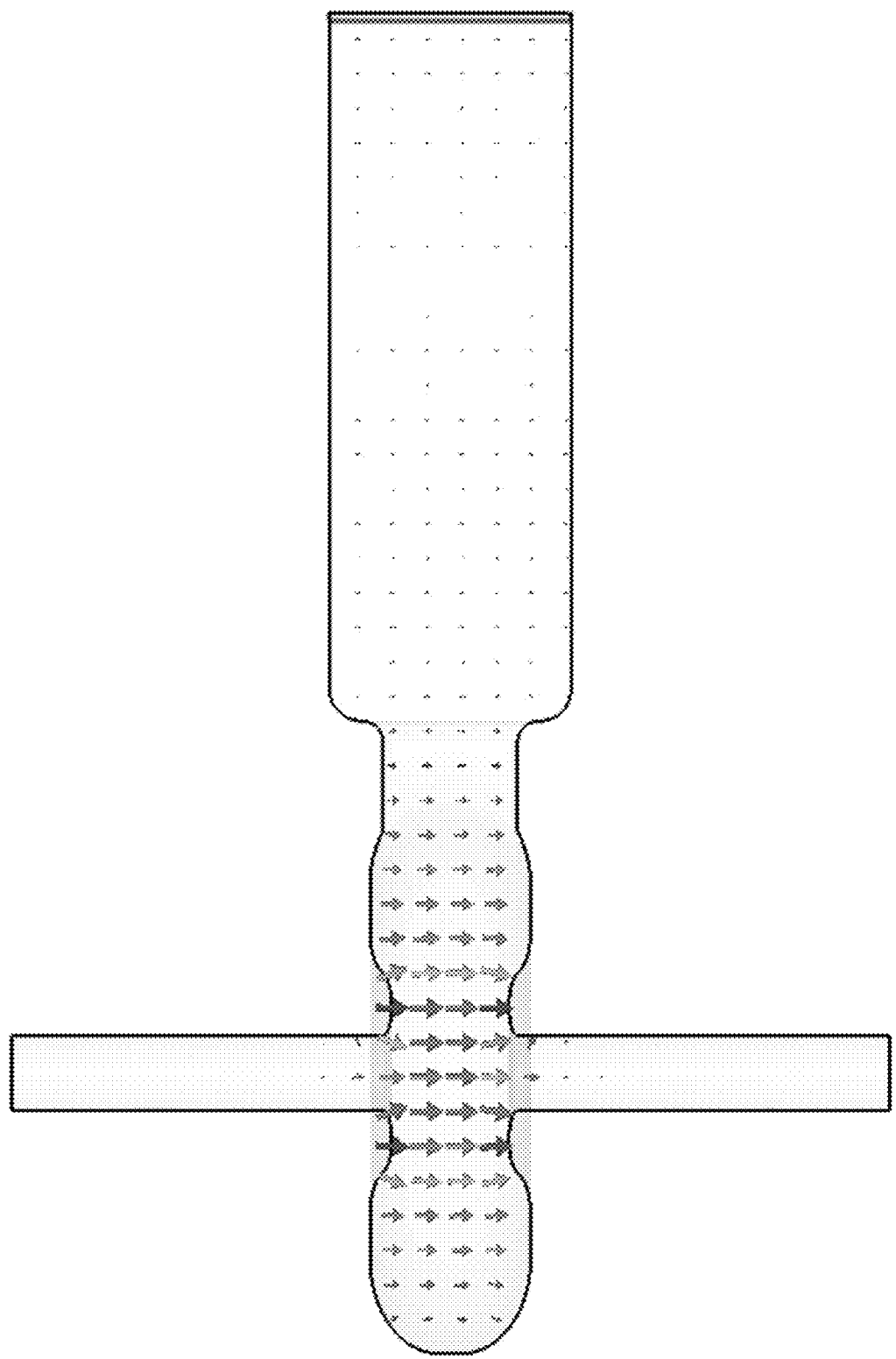
FIG. 11B schematically depicts the electric field distribution of the proton cavity in FIG. 11A.
Figure 12:
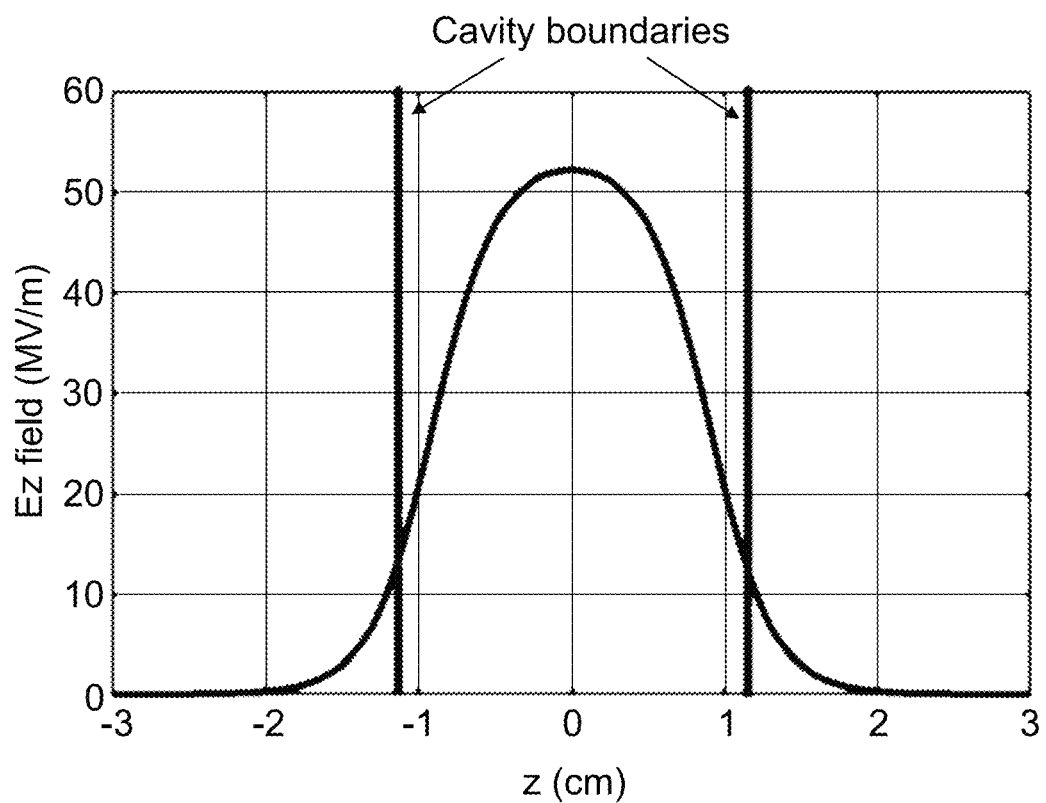
FIG. 12 graphically depicts the electric field distribution of the proton cavity in FIG. 11A.

FIG. 11A shows an exemplary proton cavity with coupler for use in a therapy system, in accordance with some embodiments. In the embodiment shown, the cavity length is about 2.4 cm, the peak E field is. $26.1\sqrt{P/(100KW)}$, and the H field enhancement is 1.35. It is appreciated that the cavity with coupler can be designed according to various other parameters as desired. FIG. 11B schematically depicts the electric field distribution of the proton cavity in FIG. 11A. The longitudinal electric field with an input power of 400 kW. FIG. 12 graphically depicts the electric field distribution of the proton cavity in FIG. 11A, relative cavity boundaries.

Figure 13B:
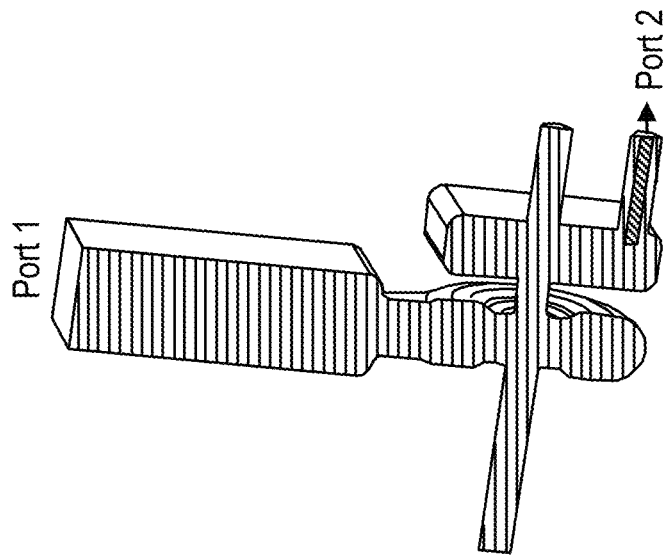
FIGS. 13A-13B shows an exemplary complete single cavity test design and cross-section, respectively, for use in a therapy system, in accordance with some embodiments.
Figure 13A:
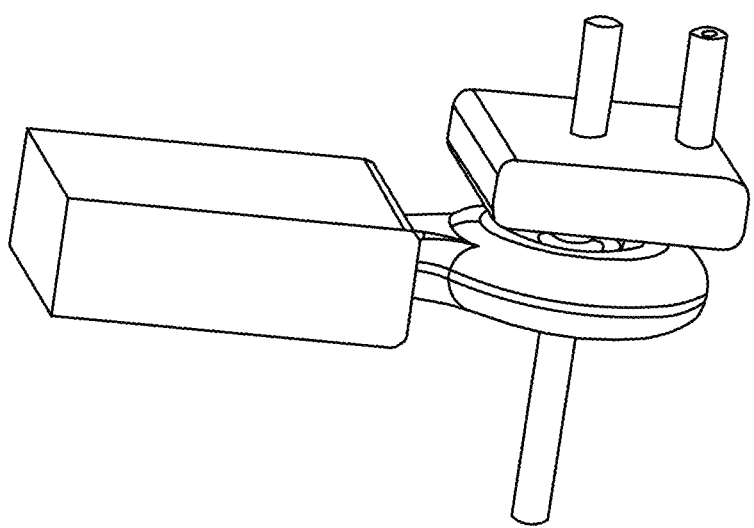
Figure 14:
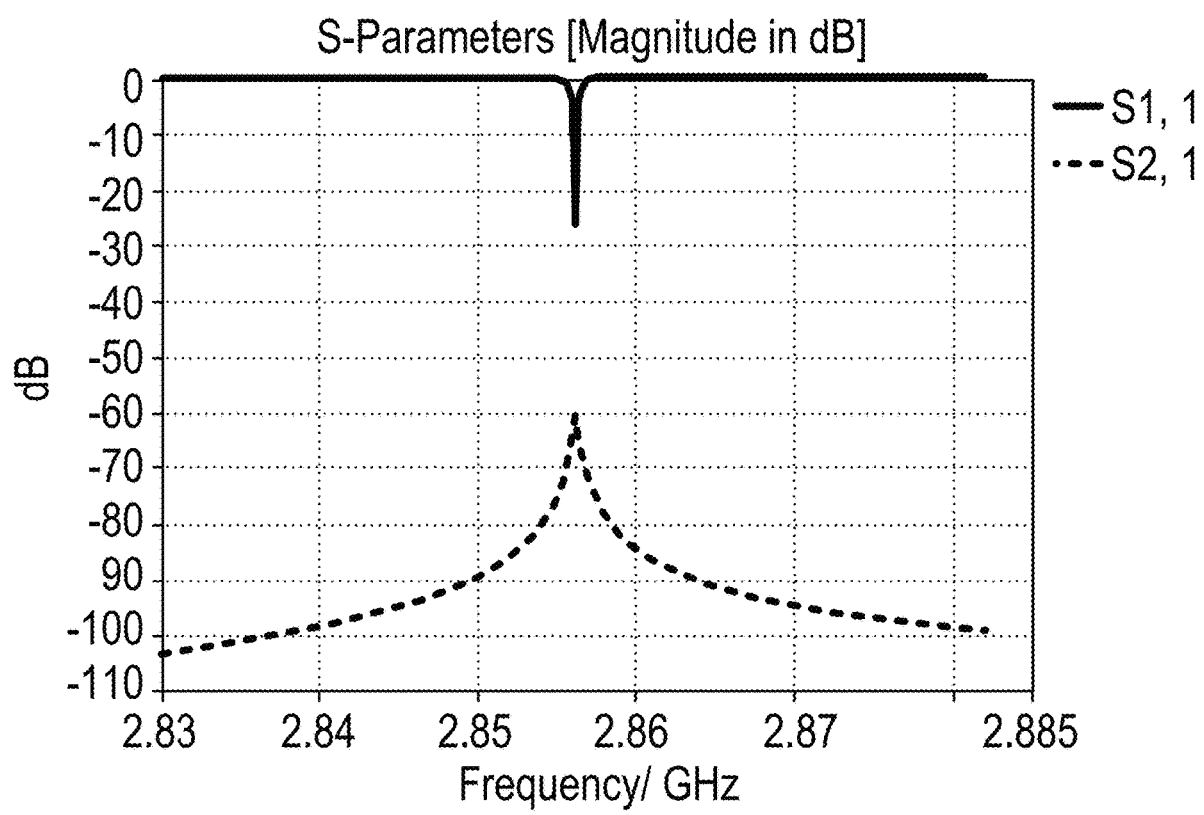
FIG. 14 shows the associated S-parameters.

FIGS. 13A-13B shows an exemplary complete single cavity test design and cross-section, respectively, for use in a therapy system, in accordance with some embodiments. FIG. 14 shows the associated S-parameters.

Figure 15A:
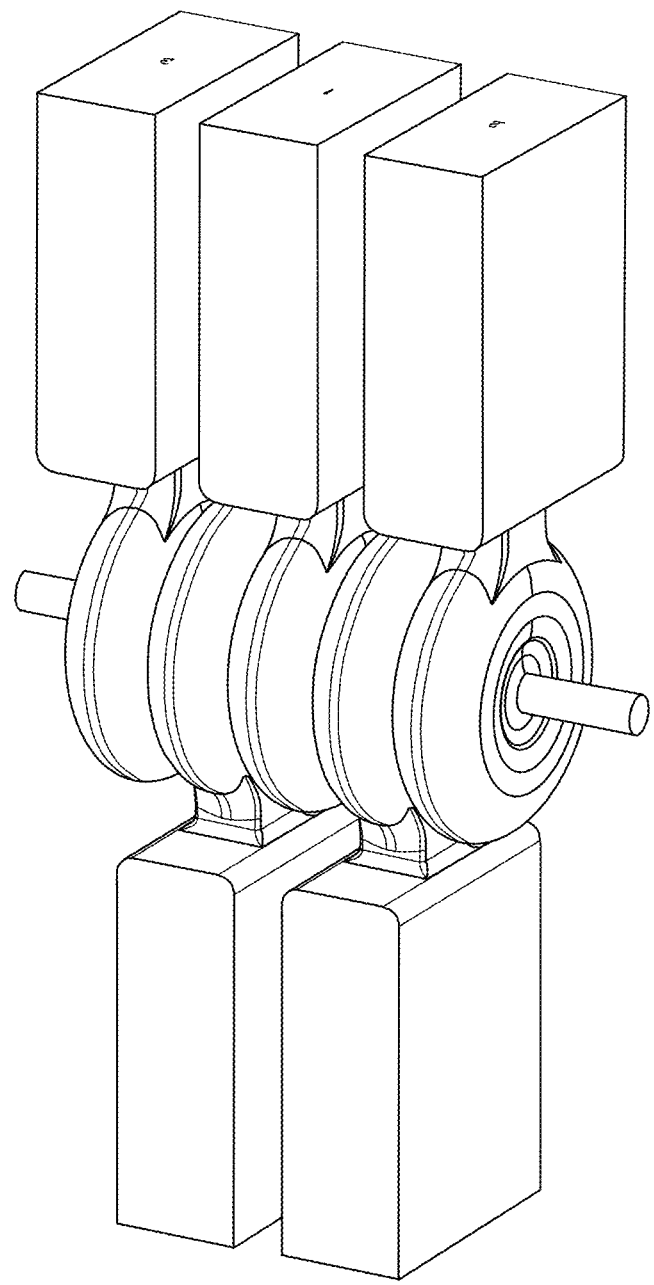
FIG. 15A shows an exemplary multi-cell design for use in a therapy system, in accordance with some embodiments.
Figure 15B:
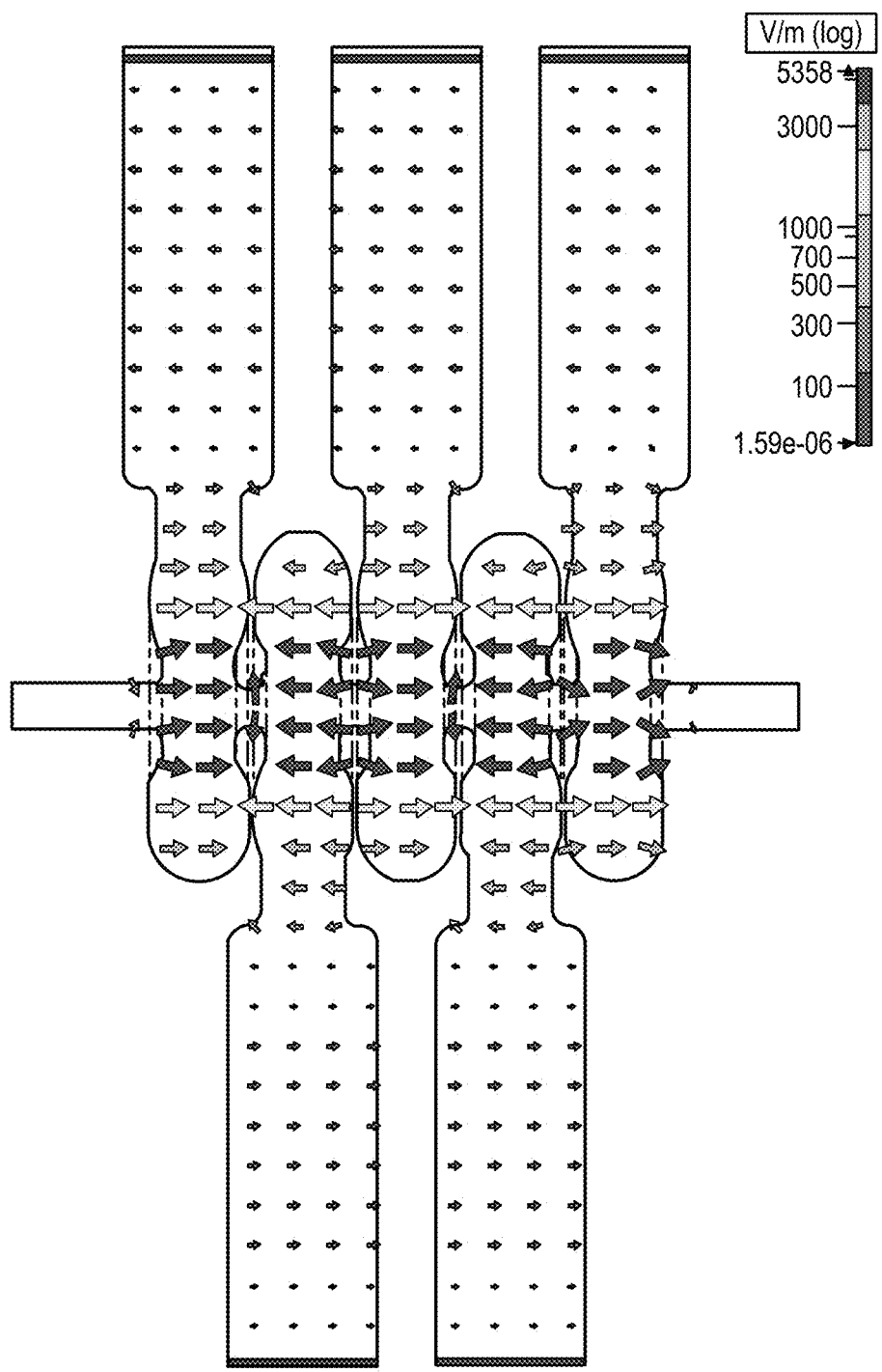
FIG. 15B schematically depicts the electric field distribution of the proton cavity in FIG. 15A.
Figure 16:
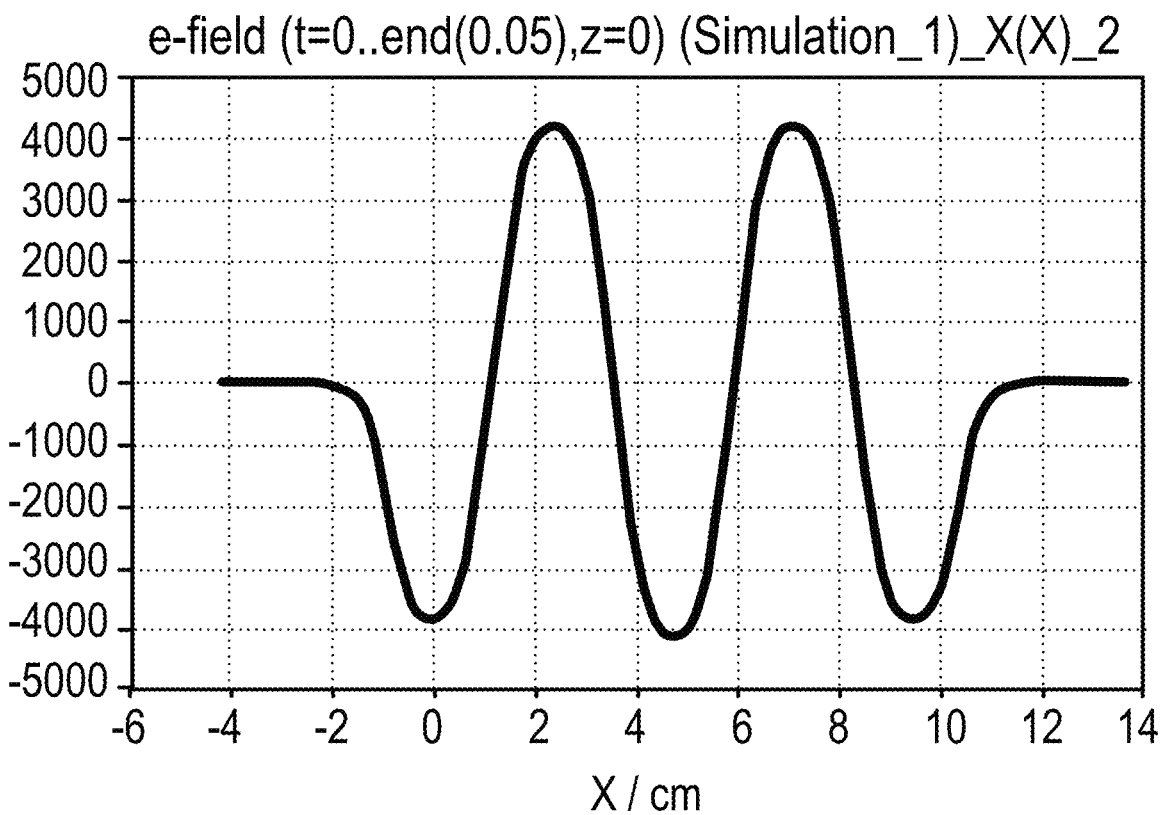
FIG. 16 graphically depicts the electric field distribution of the proton cavity in FIG. 15A.

FIG. 15A shows an exemplary multi-cell design for use in a therapy system, in accordance with some embodiments. In the embodiment shown, the multi-cell design includes five cells. This design can utilize multiple differing driving schemes, for example: driving all cells with input RF pulses, driving with a 180 degree difference between neighboring cells; and driving with equal power in all ports. FIG. 15B schematically depicts the electric field distribution of the proton cavity in FIG. 15A. FIG. 16 graphically depicts the electric field distribution of the proton cavity in FIG. 15A.

Figure 17:
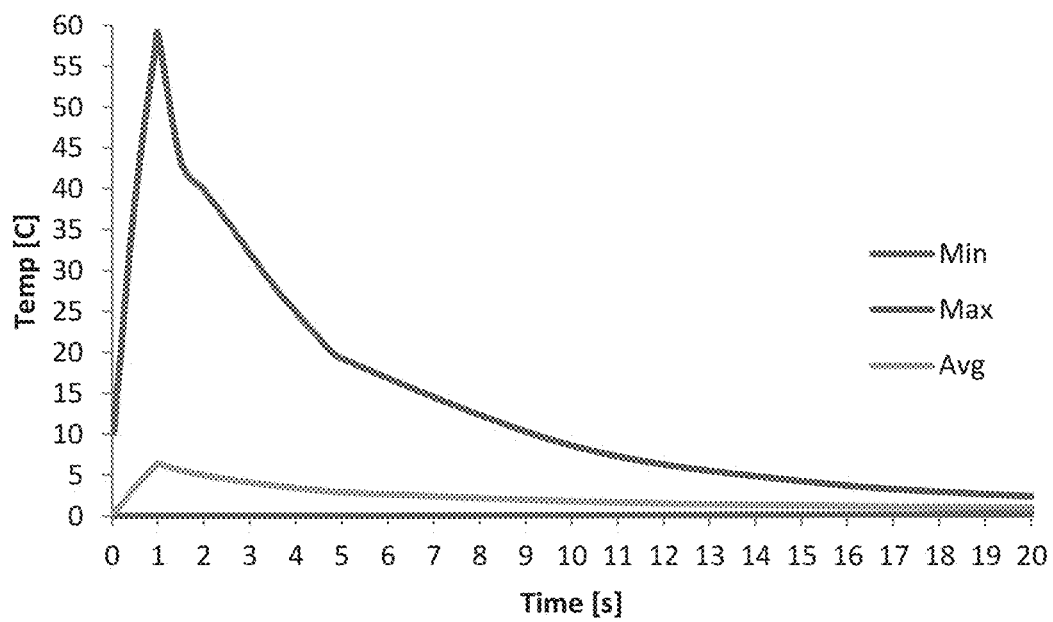
FIG. 17 graphically depicts simulation results of an exemplary five cell cavity, in accordance with some embodiments.
Figure 18:
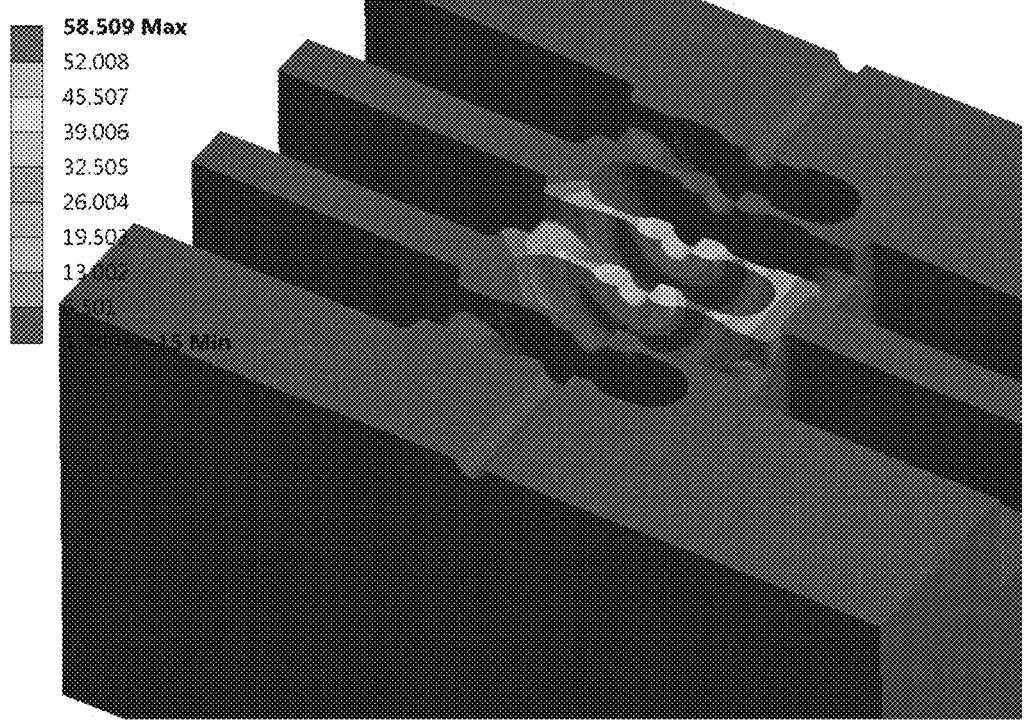
FIG. 18 depicts a thermal model of the center cell of a five cell cavity, in accordance with some embodiments.

FIG. 17 graphically depicts simulation results (only of center cell) of an exemplary five cell cavity, in accordance with some embodiments. In this embodiment, the input power of 10 kW, the mass is 45.6 kg, the initial temperature is 0 degrees Celsius, no cooling is applied and the peak temperature rise is 58.5 degrees Celsius. FIG. 18 depicts a thermal model of the center cell of a five cell cavity in FIG. 17.

Figure 19:
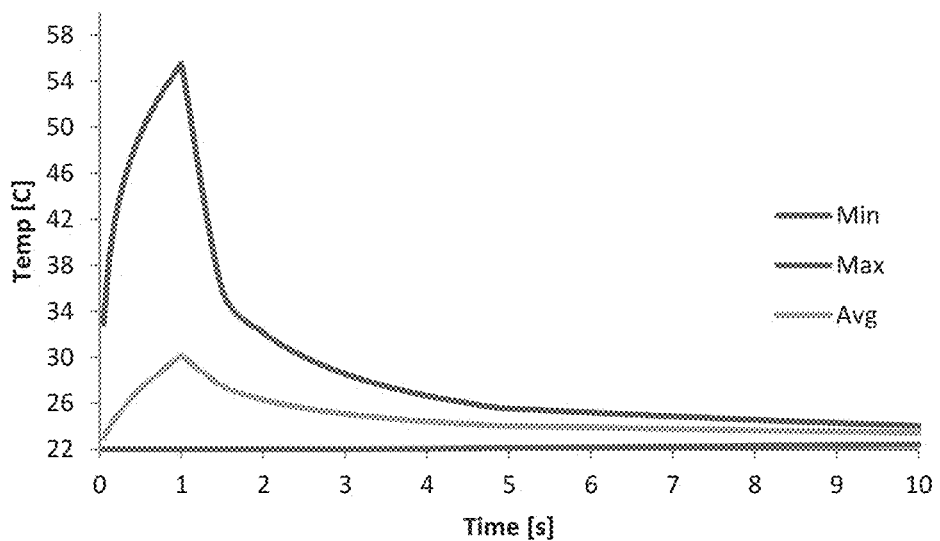
FIG. 19 graphically depicts simulation results of an exemplary single cell cavity, in accordance with some embodiments.
Figure 20:
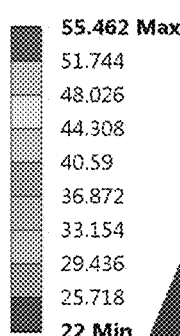
FIG. 20 depicts a thermal model of the single cell cavity, in accordance with some embodiments.

FIG. 19 graphically depicts simulation results of an exemplary single cell cavity, in accordance with some embodiments. In this embodiment, the input power is 10 KW, the mass is 23.3 kg, the initial temperature is 22 degrees Celsius, no cooling is applied, and the peak temperature rise is 33.5 degrees Celsius. FIG. 20 depicts a thermal model of the single cell cavity, in accordance with some embodiments.

Figure 21:
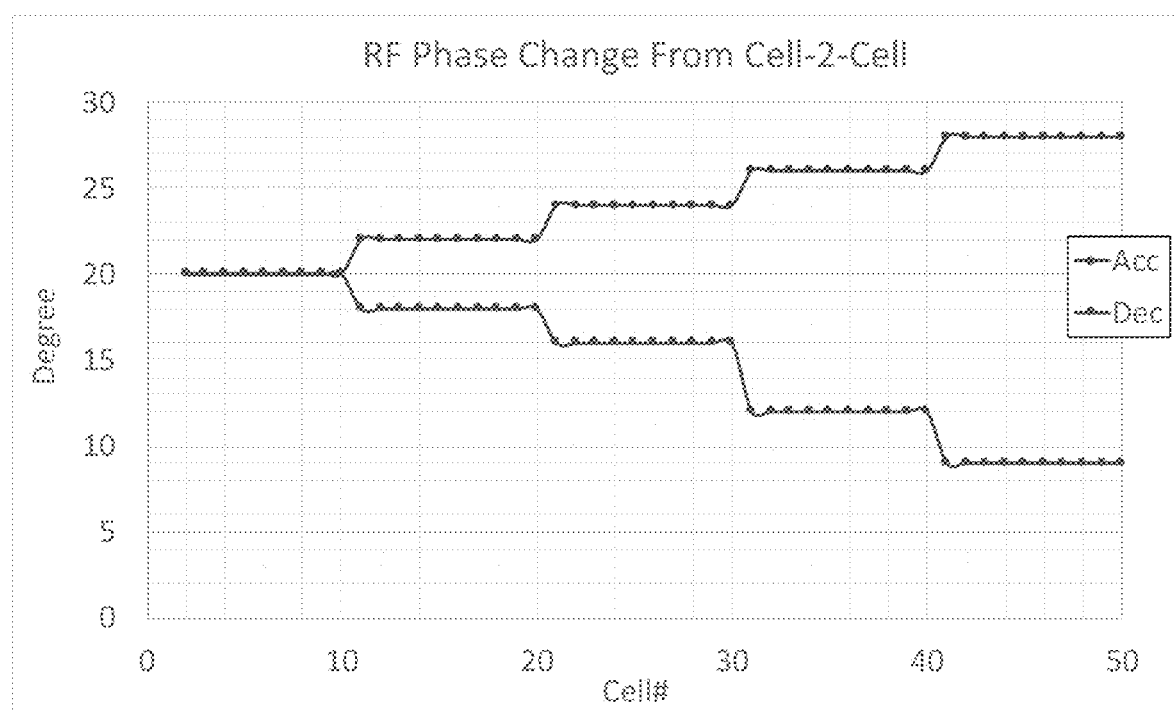
FIG. 21 depicts beam dynamics of acceleration and deceleration, in accordance with some embodiments.

FIG. 21 depicts beam dynamics of acceleration and deceleration, in accordance with some embodiments. In the embodiments shown, the initial beta is 0.5066 (150 MeV); the DeltaE is 30 MeV (gamma*beta(180): 0.649 (beta=0.544); gamma*beta(120): 0.522 (beta=0.463)); and the gradient is 30 MV/m.

Figure 22:
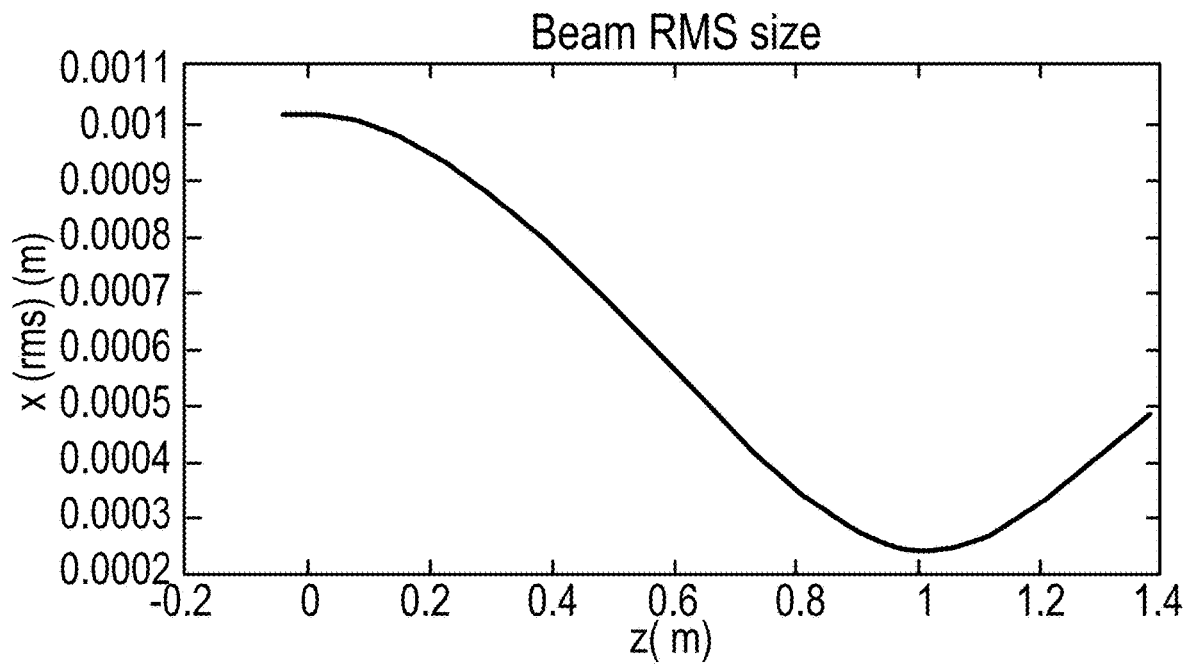
FIGS. 22-23 graphically show proton beam acceleration, in accordance with some embodiments.
Figure 23:
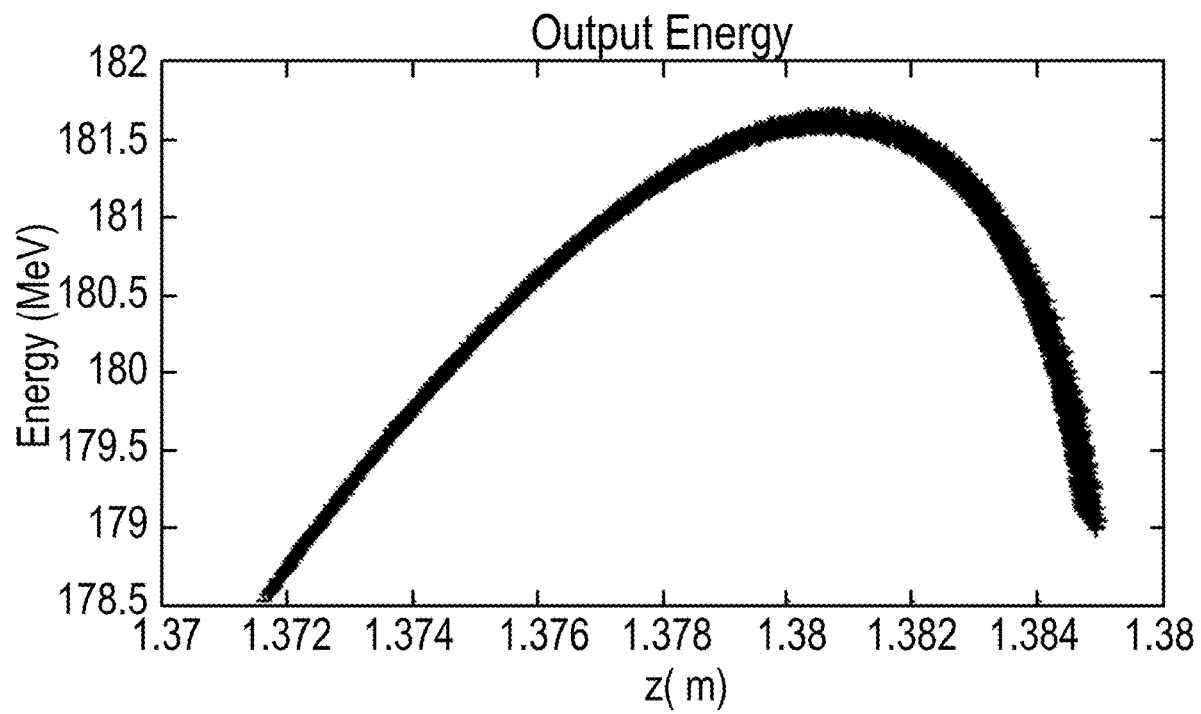

FIGS. 22-23 graphically shows proton beam acceleration for an initial beam length of 7 mm (full), an initial beta of 0.5066 (150 MeV) and an initial beam size (RMS) of 1 mm.

Figure 24:
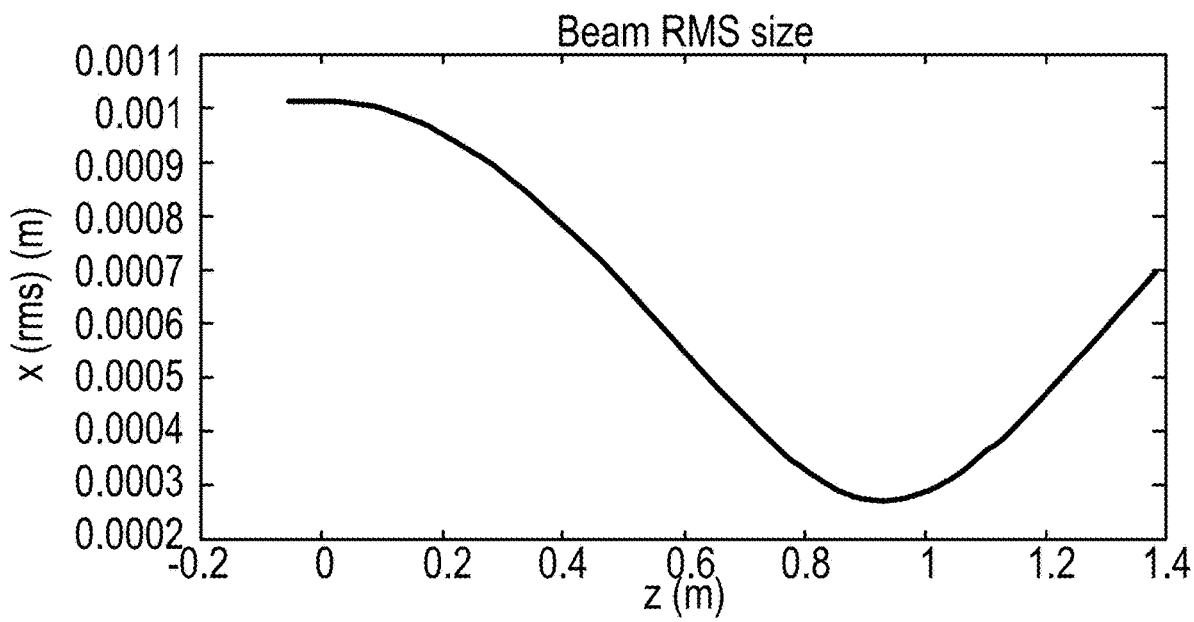
FIGS. 24-25 graphically show proton beam deceleration, in accordance with some embodiments.
Figure 25:
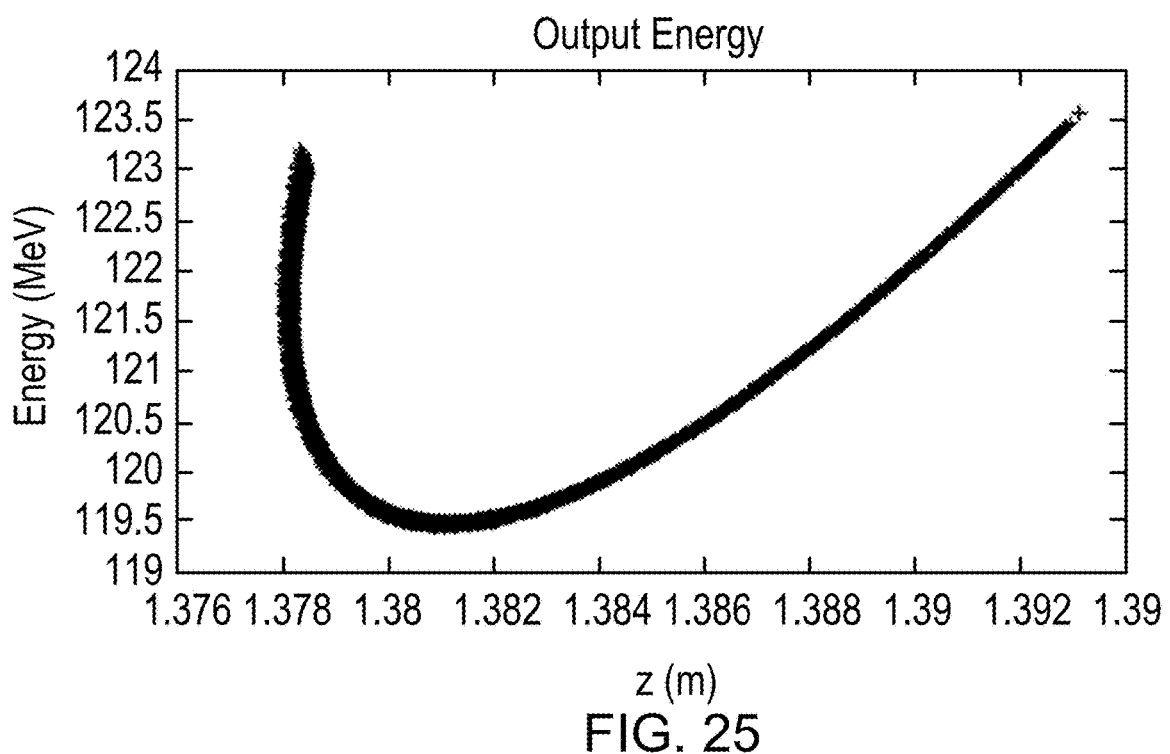

FIGS. 24-25 graphically show proton beam deceleration for an initial beam length of 7 mm (full), an initial beta of 0.5066 (150 MeV), an initial beam size (RMS) of 1 mm.

Figure 26:
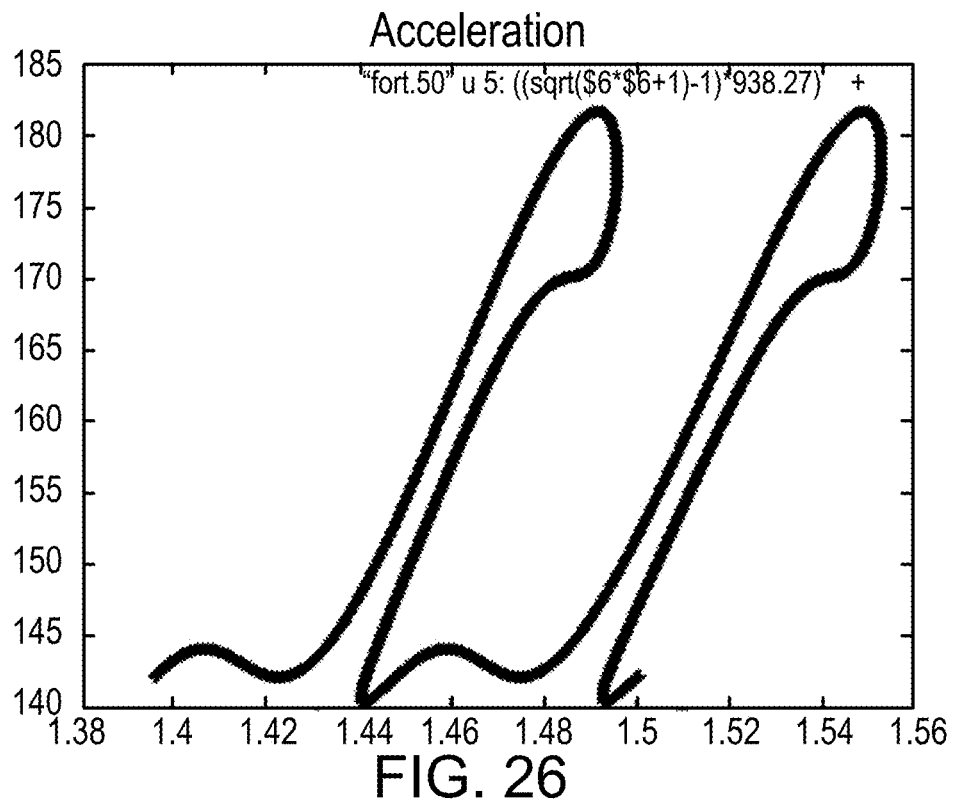
FIGS. 26-27 graphically show proton beam acceleration and deceleration, respectively, of a long bunch of two periods, in accordance with some embodiments.
Figure 27:
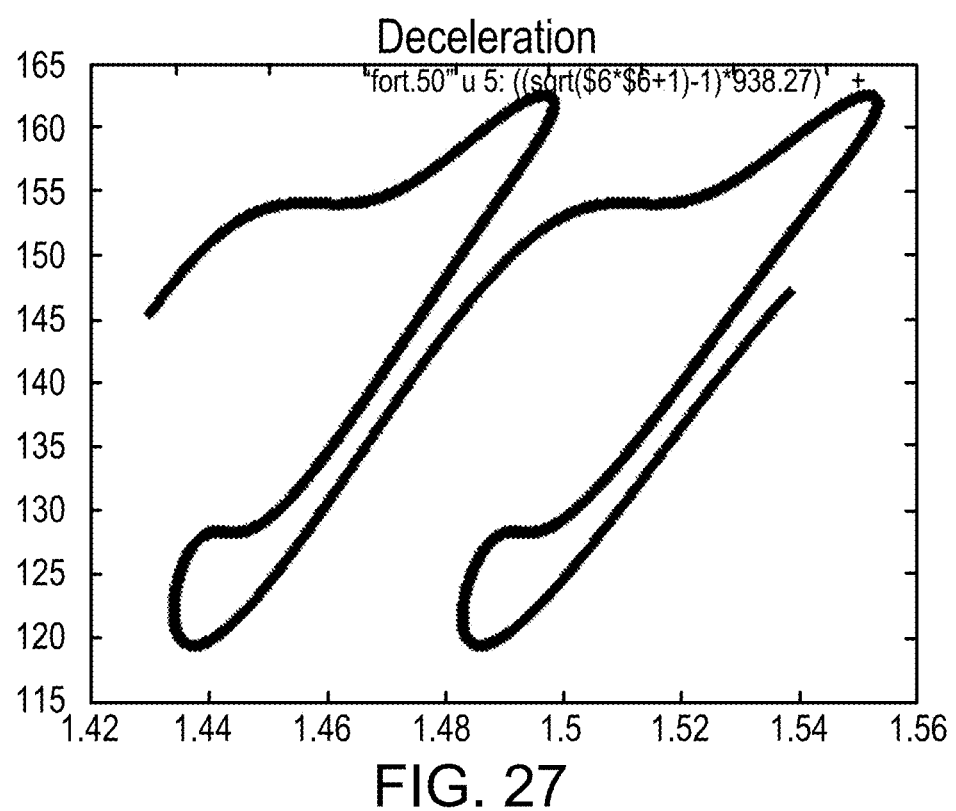

FIGS. 26-27 graphically show proton beam acceleration and deceleration of a long bunch over two periods.

Figure 28:
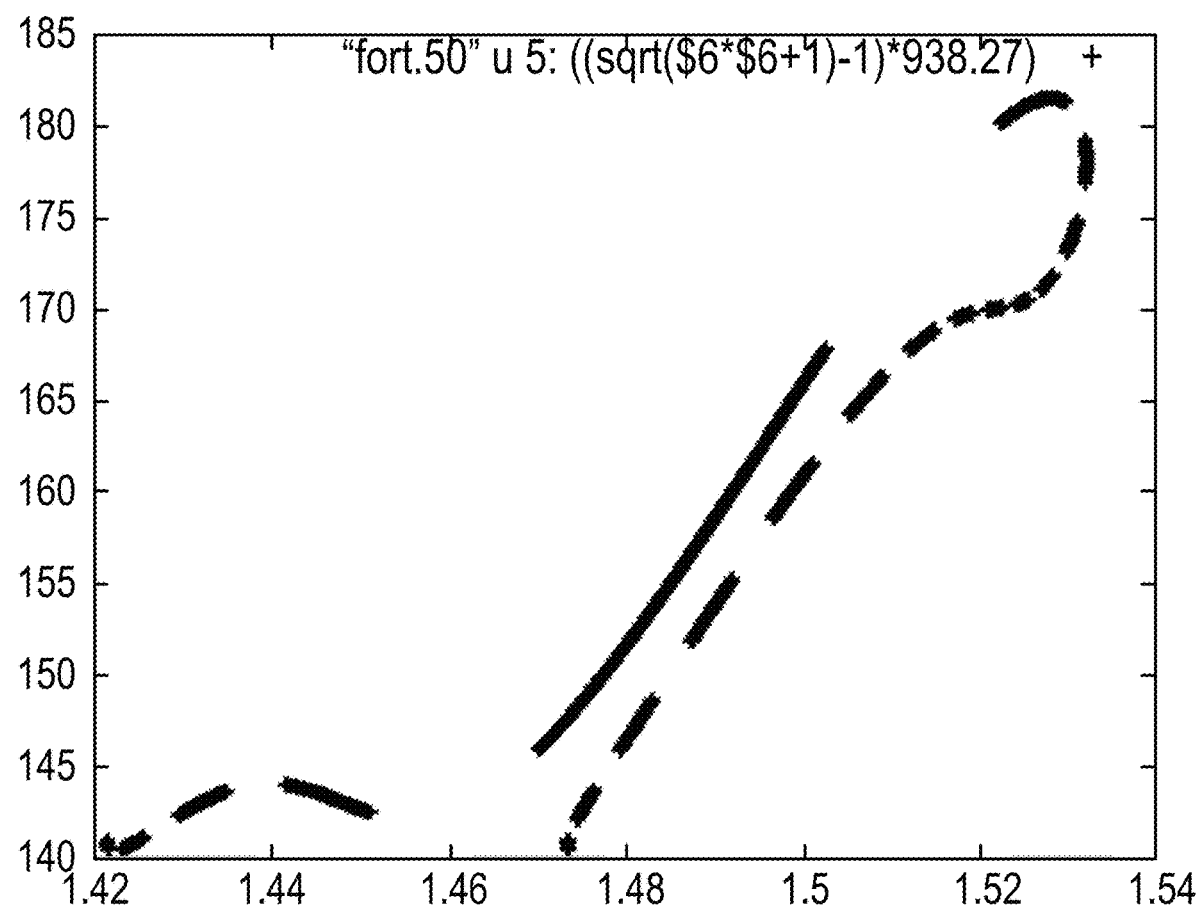
FIG. 28 graphically shows an estimation of required bunch length, in accordance with some embodiments.

FIG. 28 graphically shows an estimation of required bunch length for acceleration of 1" RF" cycle (beta=0.5066), and 10 degree segments, 10 degrees apart.

Figure 29A:
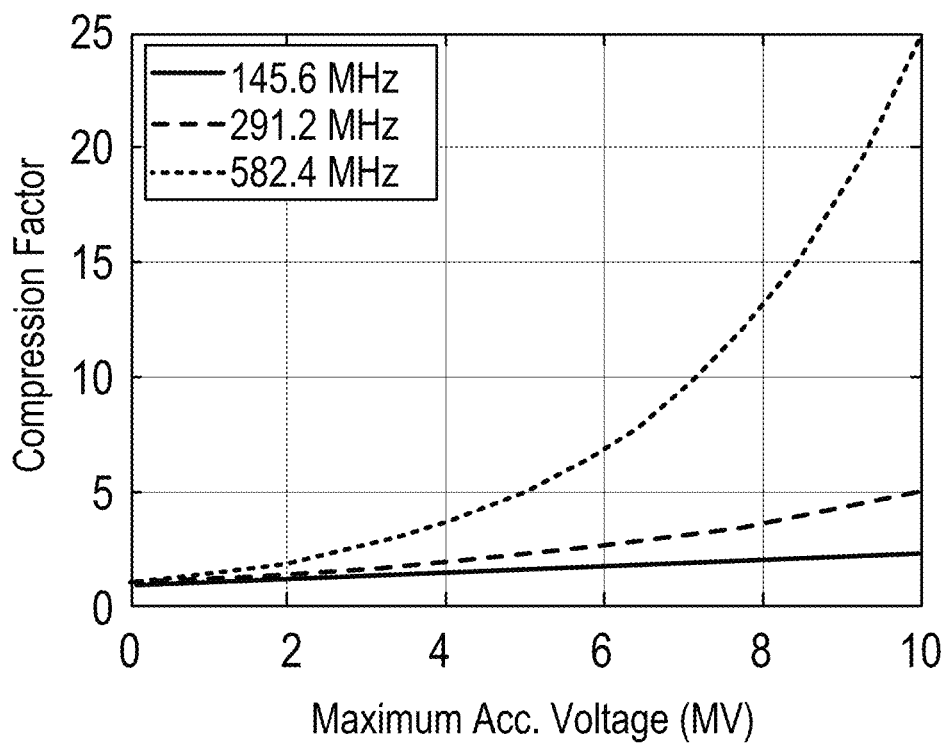
FIG. 29A graphically show a bunch compression factor at a zero-crossing cavity of a bunch compressor, in accordance with some embodiments.
Figure 29B:
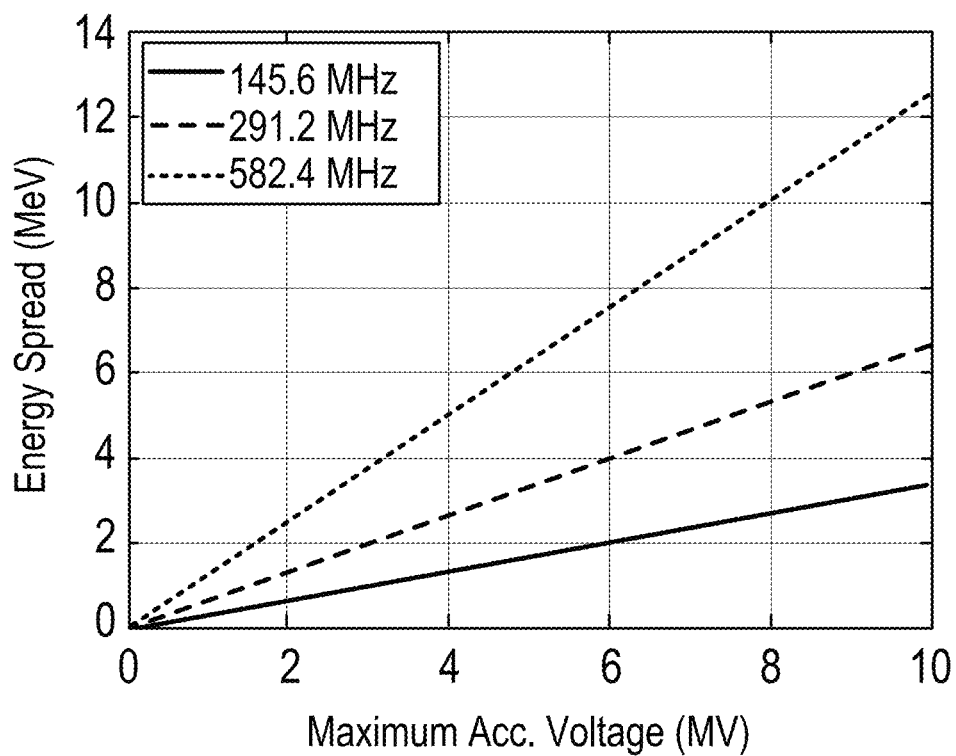
FIG. 29B graphically shows energy spread caused by the bunch compressor, in accordance with some embodiments.

FIG. 29A graphically shows a bunch compression factor at a zero-crossing cavity of a bunch compressor, in accordance with some embodiments. In one aspect, the bunch compression factor should be at a zero-crossing cavity with a maximum accelerating voltage of V0 at different RF frequencies. In this embodiment, the bunch length before chirper cavity is 56 mm and the drift space is 5 m. FIG. 29B graphically shows energy spread caused by the bunch compressor. In this embodiment, the energy spread: $\Delta E = 2eV\_0 \sin(k\sigma\_z/2\beta)$.

Figure 30:
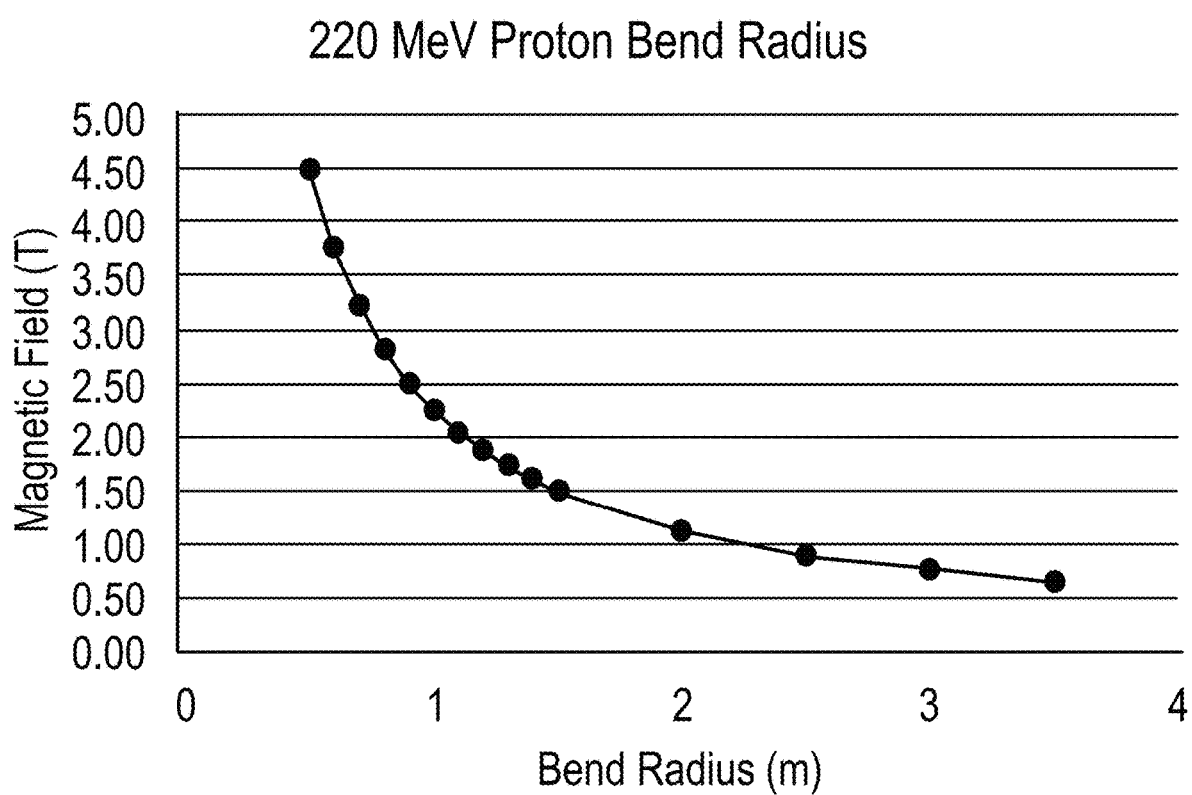
FIG. 30 graphically shows magnetic field versus bend radius in a permanent magnetic gantry, in accordance with some embodiments.

FIG. 30 graphically shows magnetic field versus bend radius in a permanent magnetic gantry for 220 MeV protons, in accordance with some embodiments. It is appreciated that the system can be designed to operate at other energies as desired.

Figure 31:
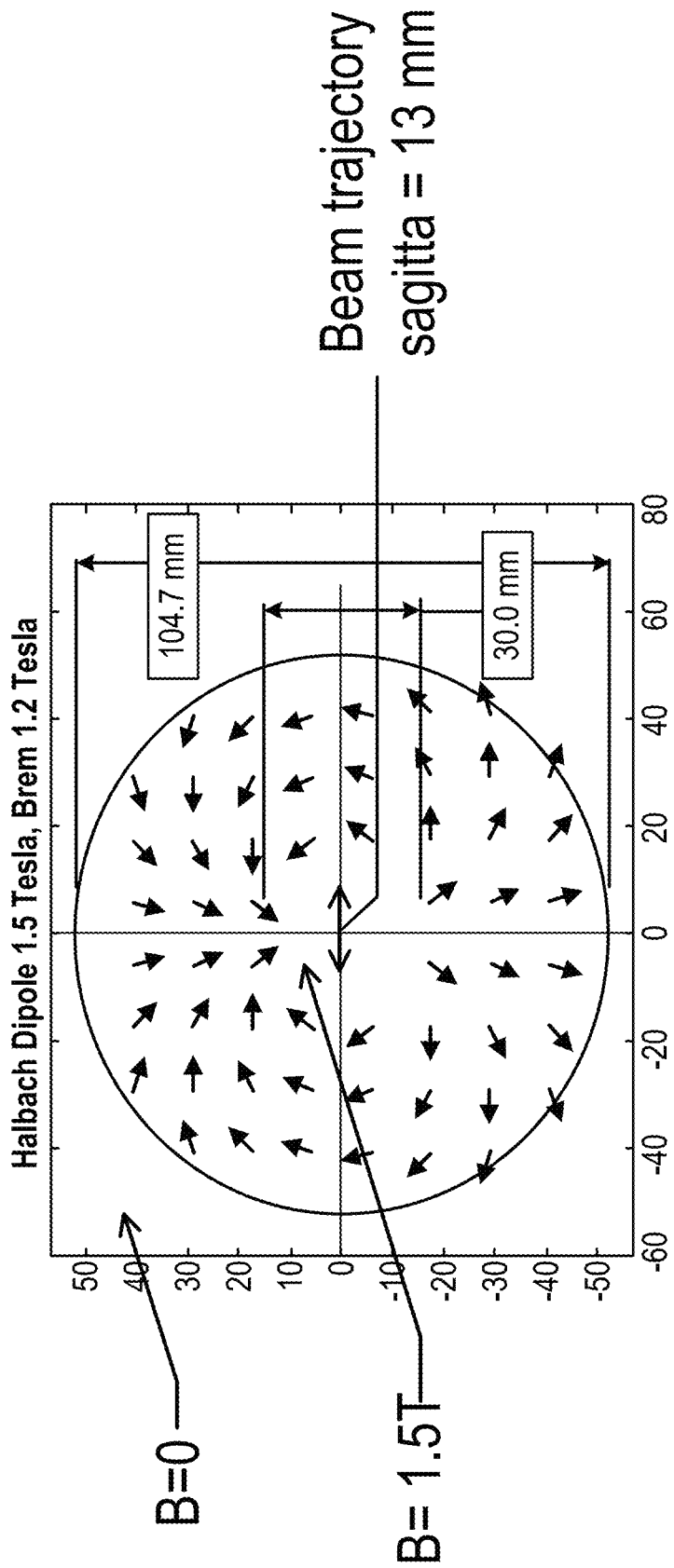
FIG. 31 graphically depicts the field of a proton therapy gantry having 90 degree bends with continuously rotating field, in accordance with some embodiments.

FIG. 31 graphically depicts the field of a proton therapy gantry having 90 degree bends, in accordance with some embodiments. This depiction is an estimate based on Halbach rings with continuously rotating field. A realistic magnet assembly with support structure would weight about 300 kb.

Figure 32A:
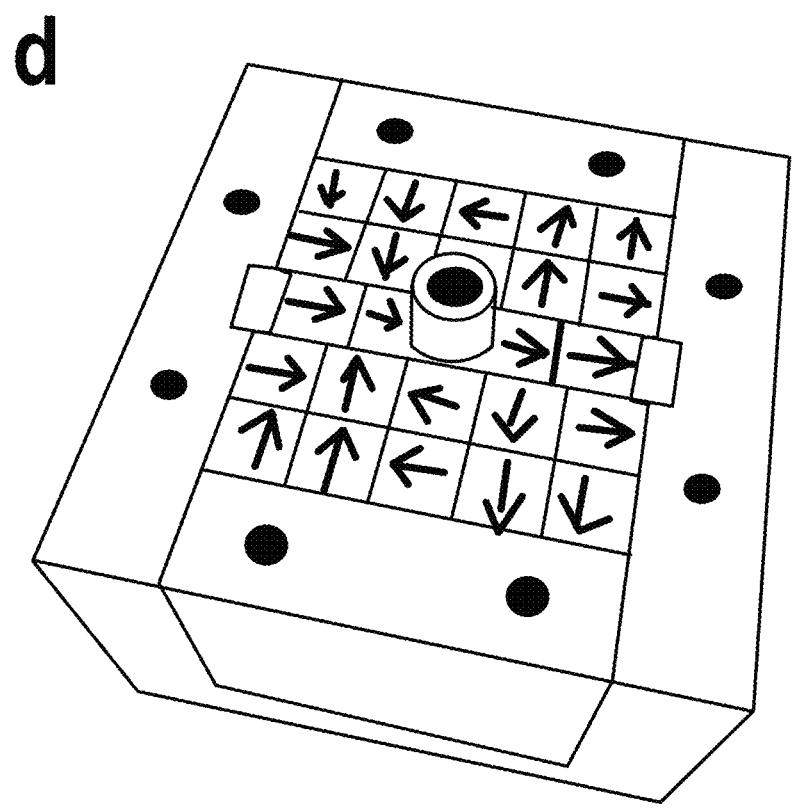
FIG. 32A-32B shows an exemplary dipole magnet and graphical depiction of magnetic field, in accordance with some embodiments.
Figure 32B:
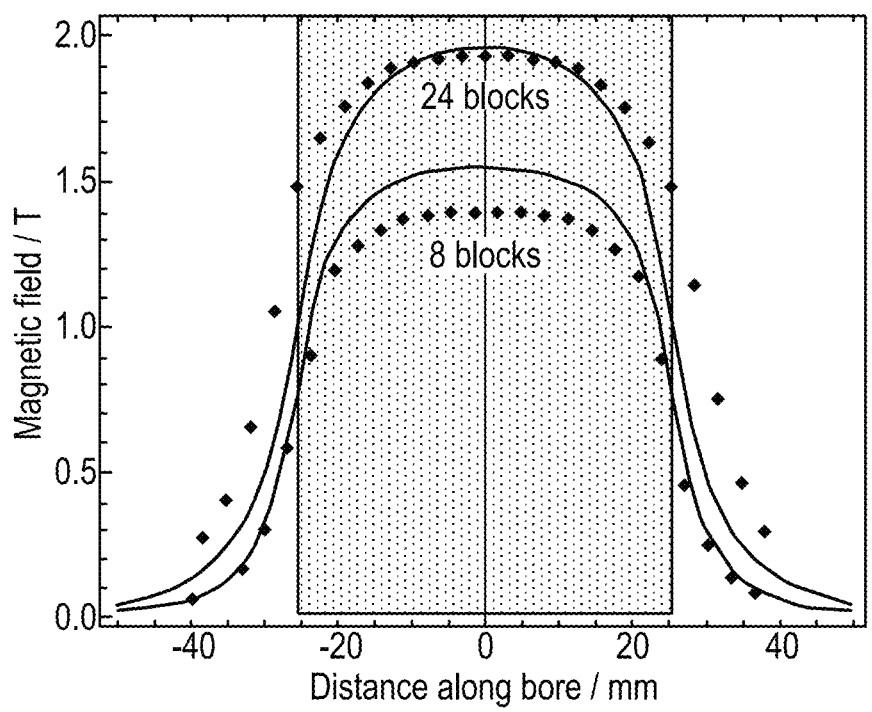

FIG. 32A-32B shows an exemplary dipole magnet and graphical depiction of magnetic field, in accordance with some embodiments. This demonstrates a high field with an even simpler configuration. The dipole magnet utilizes a 1.95 T 7.5 mm bore. A support gantry would require about three 90 degree bends on the order of about 1 ton.

Figure 33:
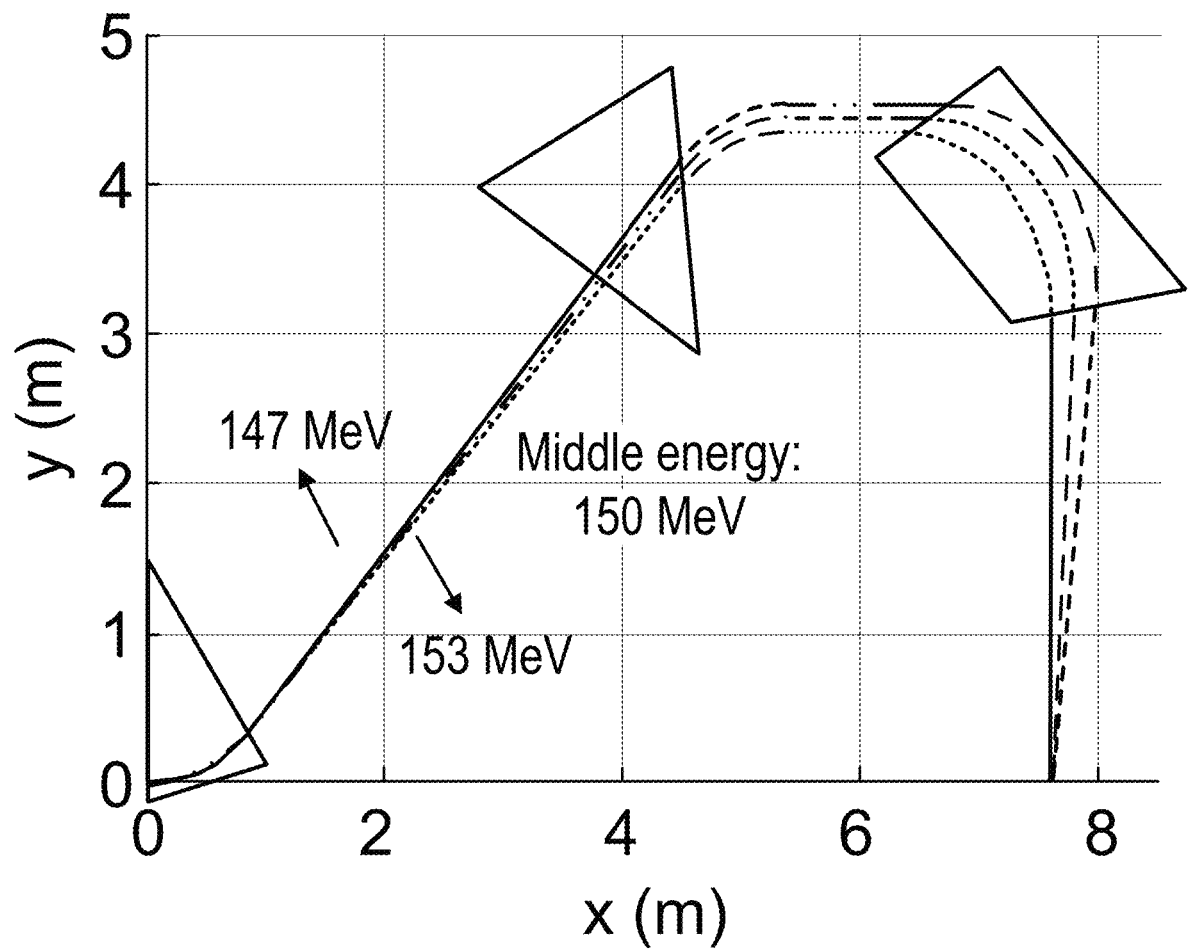
FIG. 33 shows an exemplary gantry layout with three bending magnets, in accordance with some embodiments.

FIG. 33 shows an exemplary gantry layout with bending magnets, in accordance with some embodiments. In this embodiment, the gantry utilizes three bending magnets of B=1.5 T. It is appreciated however that differing configurations and strengths of bending magnets could be used depending on the energy levels being used and the gantry layout.

Although the above descriptions provide specific examples and values, it is appreciated that the concepts herein are not so limited. The examples herein are illustrative of broader concepts and that these components can be designed according to various parameters in order to achieve differing energies or scan capabilities as desired. Many possible variations and modifications to the invention will be apparent to one skilled in the art upon consideration of this disclosure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A treatment system that directs a hadron therapy beam to a target, the system comprising:
   a hadron source and accelerator providing the hadron beam at a desired energy level;
   an RF energy modulator disposed along a beamline of the hadron beam;
   an RF deflector disposed along the beamline, the RF deflector configured to scan the hadron beam transversally; and
   a magnetic quadrupole disposed along the beamline.

2. The system of claim 1 wherein the combination of energy modulation from the RF energy modulator and steering by the RF deflector provide 3D scanning of the target.

3. The system of claim 1 wherein the system is configured to scan a full irradiation dose of a liter scale tumor in less than one second.

4. The system of claim 1, further comprising:
a transfer portion disposed along the beamline between the hadron source and the RF energy modulator, where the transfer portion includes one or more permanent magnets for bending the hadron beam from the hadron source and directing the hadron beam to the RF energy modulator.

5. The system of claim 1 wherein the RF energy modulator and the RF deflector are powered with a plurality of klystrons.

6. The system of claim 5 wherein the plurality of klystrons feed a plurality of corresponding cavity cells, each klystron feeding one cell.

7. The system of claim 5 wherein each single klystron is capable of providing 300 kW.

8. The system of claim 1 wherein the magnetic quadrupole comprises a plurality of permanent magnet quadrupoles in a stack.

9. The system of claim 8 wherein the plurality of permanent magnet quadrupoles are stacked with increasing bore diameter.

10. The system of claim 8 wherein the plurality of permanent magnet quadrupoles includes three permanent magnets stacked together.

11. The system of claim 8 wherein the permanent magnet quadrupole is rotatable.

12. The system of claim 1 wherein the system is configured to operate at a fixed energy for 150 MeV protons or greater.

13. The system of claim 1 wherein the system is configured to provide a bend of the beamline of at least 90 degrees between the hadron source and the target.

14. The system of claim 13 wherein the system is configured with at least three bending magnets so as to provide the bend of at least 90 degrees along the beamline.

* * * * *